US012023498B2

(12) United States Patent
Rockley et al.

(10) Patent No.: US 12,023,498 B2
(45) Date of Patent: Jul. 2, 2024

(54) OCULAR THERAPY MODES AND SYSTEMS

(71) Applicant: BIOVISICS MEDICAL, INC., Delano, MN (US)

(72) Inventors: Paul Rockley, Corona Del Mar, CA (US); James R. Chiapetta, Delano, MN (US)

(73) Assignee: Biovisics Medical, Inc., Delano, MN (US)

( * ) Notice: Subject to any disclaimer, the term of this patent is extended or adjusted under 35 U.S.C. 154(b) by 0 days.

(21) Appl. No.: 17/626,787

(22) PCT Filed: Jul. 8, 2020

(86) PCT No.: PCT/US2020/041166
§ 371 (c)(1),
(2) Date: Jan. 12, 2022

(87) PCT Pub. No.: WO2021/011255
PCT Pub. Date: Jan. 21, 2021

(65) Prior Publication Data
US 2022/0296899 A1 Sep. 22, 2022

Related U.S. Application Data

(60) Provisional application No. 62/873,450, filed on Jul. 12, 2019.

(51) Int. Cl.
*A61N 1/04* (2006.01)
*A61N 1/36* (2006.01)

(52) U.S. Cl.
CPC ....... *A61N 1/36046* (2013.01); *A61N 1/0496* (2013.01)

(58) Field of Classification Search
CPC .............. A61N 1/36046; A61N 1/0496; A61N 1/0456; A61N 1/0484; A61N 1/0492; A61N 1/0452
See application file for complete search history.

(56) References Cited

U.S. PATENT DOCUMENTS 2,283,752 A 5/1942 Gonsett
2,527,947 A 10/1950 Loos
(Continued)

FOREIGN PATENT DOCUMENTS

CN 1096460 A 12/1994
DE 202012003100 U1 10/2012
(Continued)

OTHER PUBLICATIONS

Chlaihawi et al.; "Development of Printed and Flexible Dry ECG Electrodes", Sensing and Bio-Sensing Research, vol. 20, pp. 9-15, 2018.
(Continued)

*Primary Examiner* — Ankit D Tejani
*Assistant Examiner* — Joshua Brendon Solomon
(74) *Attorney, Agent, or Firm* — Seager, Tufte & Wickhem, LLP

(57) ABSTRACT

Methods, systems and apparatuses for delivering electrical or other therapy in the vicinity of the eye. One or more electrodes are positioned on or near the eye, such as contacting the superior or inferior eyelids, on the conjunctiva or medial or lateral canthus, on or inside the nose, or on the forehead. A remote or return electrode is optionally positioned elsewhere on the patient on the torso, neck, back, a limb, an extremity, on the back or side of the head, or near the ear, mandible or temple. A variety of pulse generator positions and support apparatuses are disclosed as well. The pulse generator is used to deliver one or more of therapy or diagnostic electrical pulses to the patient to address a condition of the eye.

19 Claims, 14 Drawing Sheets

(56) References Cited

U.S. PATENT DOCUMENTS

| | | |
|---|---|---|
| 2,760,483 A | 8/1956 | Tassicker |
| 3,376,870 A | 4/1968 | Yamamoto et al. |
| 3,669,119 A | 6/1972 | Symmes |
| D246,529 S | 11/1977 | Willard |
| 4,162,542 A | 7/1979 | Frank |
| D280,670 S | 9/1985 | Fireman |
| 4,551,149 A | 11/1985 | Scairra |
| 4,614,193 A | 9/1986 | Liss et al. |
| 4,628,933 A | 12/1986 | Michelson |
| 4,664,117 A | 5/1987 | Beck |
| 4,712,558 A | 12/1987 | Kidd et al. |
| 4,979,811 A | 12/1990 | Boyer |
| 5,024,223 A | 6/1991 | Chow |
| 5,109,844 A | 5/1992 | De Juan et al. |
| 5,147,284 A | 9/1992 | Fedorov et al. |
| 5,154,174 A | 10/1992 | Hawlina |
| 5,193,540 A | 3/1993 | Schulman et al. |
| 5,263,200 A | 11/1993 | Miller |
| 5,522,864 A | 6/1996 | Wallace et al. |
| 5,556,423 A | 9/1996 | Chow et al. |
| 5,597,381 A | 1/1997 | Rizzo, III |
| 5,643,330 A | 7/1997 | Holsheimer et al. |
| 5,836,996 A | 11/1998 | Doorish |
| 5,843,147 A | 12/1998 | Testerman et al. |
| 5,865,839 A | 2/1999 | Doorish |
| 5,873,901 A | 2/1999 | Wu et al. |
| 5,895,415 A | 4/1999 | Chow et al. |
| 5,935,155 A | 8/1999 | Humayun et al. |
| 5,944,747 A | 8/1999 | Greenberg et al. |
| 6,007,532 A | 12/1999 | Netherly |
| D421,124 S | 2/2000 | Yavitz |
| 6,035,236 A | 3/2000 | Jarding et al. |
| D425,623 S | 5/2000 | Funk |
| D429,817 S | 8/2000 | Banks |
| 6,101,411 A | 8/2000 | Newsome |
| 6,131,208 A | 10/2000 | Banks |
| 6,154,671 A | 11/2000 | Parel et al. |
| D440,660 S | 4/2001 | Sternberg |
| 6,230,057 B1 | 5/2001 | Chow et al. |
| D444,561 S | 7/2001 | Stein |
| 6,275,735 B1 | 8/2001 | Jarding et al. |
| 6,282,449 B1 | 8/2001 | Kamerling et al. |
| 6,306,075 B1 | 10/2001 | Shadduck |
| 6,324,429 B1 | 11/2001 | Shire et al. |
| 6,389,317 B1 | 5/2002 | Chow et al. |
| 6,400,989 B1 | 6/2002 | Eckmiller |
| 6,408,211 B1 | 6/2002 | Powell |
| 6,424,864 B1 | 7/2002 | Matsuura |
| 6,442,431 B1 | 8/2002 | Veraart et al. |
| 6,458,157 B1 | 10/2002 | Suaning |
| 6,515,227 B1 | 2/2003 | Massey et al. |
| 6,611,716 B2 | 8/2003 | Chow et al. |
| 6,755,530 B1 | 6/2004 | Loftus et al. |
| 6,792,314 B2 | 9/2004 | Byers et al. |
| 6,976,998 B2 | 12/2005 | Rizzo et al. |
| 6,990,377 B2 | 1/2006 | Gliner et al. |
| 7,001,608 B2 | 2/2006 | Fishman et al. |
| 7,003,354 B2 | 2/2006 | Chow et al. |
| 7,006,873 B2 | 2/2006 | Chow et al. |
| 7,031,776 B2 | 4/2006 | Chow et al. |
| 7,037,943 B2 | 5/2006 | Peyman |
| 7,043,308 B2 | 5/2006 | Cohen |
| 7,047,080 B2 | 5/2006 | Palanker et al. |
| 7,058,455 B2 | 6/2006 | Huie, Jr. et al. |
| 7,067,327 B2 | 6/2006 | Wu et al. |
| 7,130,693 B1 | 10/2006 | Montalbo |
| 7,139,612 B2 | 11/2006 | Chow et al. |
| 7,146,209 B2 | 12/2006 | Gross et al. |
| 7,147,865 B2 | 12/2006 | Fishman et al. |
| 7,158,834 B2 | 1/2007 | Paul, Jr. |
| 7,158,836 B2 | 1/2007 | Suzuki |
| 7,248,928 B2 | 7/2007 | Yagi |
| 7,251,528 B2 | 7/2007 | Harold |
| 7,306,621 B1 | 12/2007 | Halla et al. |
| 7,321,796 B2 | 1/2008 | Fink et al. |
| 7,337,008 B2 | 2/2008 | Terasawa et al. |
| 7,398,124 B2 | 7/2008 | Fujikado et al. |
| 7,400,021 B2 | 7/2008 | Wu et al. |
| 7,447,547 B2 | 11/2008 | Palanker |
| 7,447,548 B2 | 11/2008 | Eckmiller |
| 7,458,456 B2 | 12/2008 | Hogan et al. |
| 7,556,621 B2 | 7/2009 | Palanker et al. |
| 7,877,148 B2 | 1/2011 | Chowdhury et al. |
| 7,883,535 B2 | 2/2011 | Cantin et al. |
| 7,974,699 B2 | 7/2011 | Tano et al. |
| 7,979,134 B2 | 7/2011 | Chow et al. |
| 7,981,062 B2 | 7/2011 | Chow et al. |
| 8,000,804 B1 | 8/2011 | Wessendorf et al. |
| 8,039,445 B2 | 10/2011 | Behar-Cohen et al. |
| 8,070,688 B2 | 12/2011 | Livne et al. |
| 8,190,266 B2 | 5/2012 | Ameri et al. |
| 8,197,539 B2 | 6/2012 | Nasiatka et al. |
| 8,260,428 B2 | 9/2012 | Fink et al. |
| 8,265,764 B2 | 9/2012 | Tano et al. |
| 8,306,626 B2 | 11/2012 | Chow et al. |
| 8,377,120 B2 | 2/2013 | Lipshitz et al. |
| 8,396,561 B2 | 3/2013 | Pezaris et al. |
| 8,396,562 B2 | 3/2013 | Ameri et al. |
| 8,398,692 B2 | 3/2013 | Deisseroth et al. |
| 8,433,417 B2 | 4/2013 | Flood |
| 8,478,415 B1 | 7/2013 | Halla et al. |
| 8,515,548 B2 | 8/2013 | Rofougaran et al. |
| 8,612,002 B2 | 12/2013 | Faltys et al. |
| 8,634,923 B2 | 1/2014 | Sharpee et al. |
| 8,639,345 B2 | 1/2014 | Eipper et al. |
| 8,691,877 B2 | 4/2014 | Yun et al. |
| 8,700,167 B2 | 4/2014 | Sabel |
| 8,725,266 B2 | 5/2014 | Olson et al. |
| 8,731,683 B2 | 5/2014 | Lindenthaler |
| 8,734,513 B2 | 5/2014 | Wu et al. |
| 8,771,349 B2 | 7/2014 | Schachar |
| 8,788,041 B2 | 7/2014 | Yun et al. |
| 8,801,942 B2 | 8/2014 | Scorsone et al. |
| 8,824,156 B2 | 9/2014 | Tai et al. |
| 8,852,290 B2 | 10/2014 | Rowley et al. |
| 8,864,805 B2 | 10/2014 | Deisseroth et al. |
| 8,868,202 B2 | 10/2014 | Della Santina et al. |
| 8,903,495 B2 | 12/2014 | Greenberg et al. |
| 8,909,340 B2 | 12/2014 | Yun |
| 8,918,186 B2 | 12/2014 | Tiedtke |
| 8,918,188 B2 | 12/2014 | Tiedtke |
| 8,972,004 B2 | 3/2015 | Simon et al. |
| 9,002,463 B2 | 4/2015 | Tiedtke |
| 9,037,251 B2 | 5/2015 | Narayan et al. |
| 9,037,252 B2 | 5/2015 | Tiedtke |
| 9,037,255 B2 | 5/2015 | Rocke et al. |
| 9,078,743 B2 | 7/2015 | Tai et al. |
| 9,079,042 B2 | 7/2015 | Tiedtke et al. |
| 9,125,734 B2 | 9/2015 | Keller et al. |
| 9,144,608 B2 | 9/2015 | Olson et al. |
| 9,162,060 B2 | 10/2015 | Wrobel et al. |
| 9,162,061 B2 | 10/2015 | Barnes |
| 9,180,309 B2 | 11/2015 | Nirenberg et al. |
| 9,186,523 B1 | 11/2015 | Zolli |
| 9,187,745 B2 | 11/2015 | Deisseroth et al. |
| 9,199,080 B2 | 12/2015 | Gekeler et al. |
| 9,220,634 B2 | 12/2015 | Nirenberg |
| 9,220,894 B1 | 12/2015 | Zhu |
| 9,233,026 B2 | 1/2016 | Ziemeck et al. |
| 9,233,258 B2 | 1/2016 | Simon et al. |
| 9,242,067 B2 | 1/2016 | Shore et al. |
| 9,403,001 B2 | 1/2016 | Simon et al. |
| 9,302,103 B1 | 4/2016 | Nirenberg |
| 9,322,713 B2 | 4/2016 | Narayan et al. |
| 9,326,887 B2 | 5/2016 | Yun |
| 9,339,650 B2 | 5/2016 | Rezai et al. |
| 9,345,568 B2 | 5/2016 | Cho et al. |
| 9,370,348 B2 | 6/2016 | Tally et al. |
| 9,381,355 B2 | 7/2016 | Khraiche et al. |
| 9,452,289 B2 | 9/2016 | Chichilnisky et al. |
| 9,456,836 B2 | 10/2016 | Boling et al. |
| 9,468,760 B1 | 10/2016 | Lin |
| 9,498,380 B2 | 11/2016 | Berdahl et al. |
| 9,630,013 B2 | 4/2017 | Bachinski et al. |

(56) References Cited

U.S. PATENT DOCUMENTS

| | | |
|---|---|---|
| 9,636,212 B2 | 5/2017 | Tiedtke et al. |
| 9,682,232 B2 | 6/2017 | Shore et al. |
| 9,687,652 B2 | 6/2017 | Franke et al. |
| 9,697,746 B2 | 7/2017 | Barnes et al. |
| 9,737,710 B2 | 8/2017 | Fan |
| 9,737,711 B2 | 8/2017 | Twyford et al. |
| 9,789,312 B2 | 10/2017 | Fukuma et al. |
| 9,795,787 B2 | 10/2017 | Cho et al. |
| 9,821,003 B2 | 11/2017 | Yun |
| 9,821,159 B2 | 11/2017 | Ackermann et al. |
| 9,844,459 B2 | 12/2017 | Badawi |
| 9,867,988 B2 | 1/2018 | Fink et al. |
| 9,884,180 B1 | 2/2018 | Ho et al. |
| 9,895,529 B2 | 2/2018 | Tiedtke |
| 9,925,373 B2 | 3/2018 | Nirenberg |
| 9,931,506 B2 | 4/2018 | Chung et al. |
| 9,937,346 B2 | 4/2018 | Lineaweaver et al. |
| 9,950,153 B2 | 4/2018 | Wagner et al. |
| 9,956,425 B2 | 5/2018 | Peyman |
| 9,962,540 B2 | 5/2018 | Picaud et al. |
| 9,962,558 B2 | 5/2018 | Peyman |
| 9,980,388 B2 | 5/2018 | Tai et al. |
| 9,990,861 B2 | 6/2018 | Chichilnisky et al. |
| 10,010,364 B2 | 7/2018 | Harrington |
| 10,071,251 B2 | 9/2018 | Bachinski et al. |
| 10,112,048 B2 | 10/2018 | Franke et al. |
| 10,129,647 B2 | 11/2018 | Seo et al. |
| 10,347,050 B1 | 7/2019 | Wang et al. |
| 11,305,118 B2 | 4/2022 | Rockley et al. |
| 11,338,139 B2 | 5/2022 | Rockley et al. |
| 11,471,680 B2 | 10/2022 | Chiapetta et al. |
| 11,511,112 B2 | 11/2022 | Mullins et al. |
| 2003/0158588 A1 | 8/2003 | Rizzo et al. |
| 2003/0233135 A1 | 12/2003 | Yee |
| 2003/0233137 A1 | 12/2003 | Paul, Jr. |
| 2004/0106965 A1 | 6/2004 | Chow |
| 2004/0176820 A1 | 9/2004 | Paul, Jr. |
| 2005/0004625 A1 | 1/2005 | Chow |
| 2005/0049578 A1 | 3/2005 | Tu et al. |
| 2005/0137649 A1 | 6/2005 | Paul |
| 2006/0142818 A1 | 6/2006 | Chow et al. |
| 2007/0093877 A1 | 4/2007 | Beecham et al. |
| 2008/0171929 A1 | 7/2008 | Katims |
| 2008/0194531 A1 | 8/2008 | Steer et al. |
| 2009/0217938 A1 | 9/2009 | Rabe et al. |
| 2009/0287276 A1 | 11/2009 | Greenberg et al. |
| 2011/0081333 A1 | 4/2011 | Shantha et al. |
| 2012/0123501 A1 | 5/2012 | Greenberg et al. |
| 2013/0053733 A1 | 2/2013 | Korb et al. |
| 2013/0066396 A1 | 3/2013 | Gekeler et al. |
| 2013/0184782 A1 | 7/2013 | Eipper et al. |
| 2014/0257433 A1 | 9/2014 | Ackermann et al. |
| 2014/0277435 A1 | 9/2014 | Gefen |
| 2014/0324147 A1* | 10/2014 | Wagner .............. A61N 1/36046 607/141 |
| 2015/0039067 A1 | 2/2015 | Greenberg et al. |
| 2016/0051439 A1 | 2/2016 | Brown et al. |
| 2016/0121118 A1* | 5/2016 | Franke .............. A61N 1/37205 607/135 |
| 2016/0317474 A1 | 11/2016 | Aung et al. |
| 2017/0266445 A1 | 9/2017 | O'Clock |
| 2017/0354818 A1* | 12/2017 | De Toni ............. A61N 1/36046 |
| 2018/0064935 A1 | 3/2018 | Leonhardt et al. |
| 2018/0228237 A1 | 8/2018 | Zhang et al. |
| 2018/0318585 A1 | 11/2018 | Pfeifer |
| 2018/0318586 A1 | 11/2018 | Salazar |
| 2019/0001133 A1* | 1/2019 | Onarheim ............ A61N 1/0456 |
| 2019/0143116 A1* | 5/2019 | Mowery ............ A61N 1/36046 607/53 |
| 2020/0101290 A1 | 4/2020 | Rockley et al. |
| 2020/0171307 A1 | 6/2020 | Rockley et al. |
| 2020/0324114 A1 | 10/2020 | Chiapetta et al. |
| 2022/0296899 A1 | 9/2022 | Rockley et al. |

FOREIGN PATENT DOCUMENTS

| | | |
|---|---|---|
| EP | 1985332 A1 | 10/2008 |
| GB | 2246709 A | 12/1992 |
| WO | 2006086452 A1 | 8/2006 |
| WO | 2013124141 A1 | 8/2013 |
| WO | 2015095257 A2 | 6/2015 |
| WO | 2016089751 A1 | 6/2016 |
| WO | 2017048731 A1 | 3/2017 |
| WO | 2017064500 A1 | 4/2017 |
| WO | 2018013835 A1 | 1/2018 |
| WO | 2018129351 A1 | 7/2018 |
| WO | 2018208009 A1 | 11/2018 |
| WO | 2020264263 A1 | 12/2020 |
| WO | 2021011255 A1 | 1/2021 |

OTHER PUBLICATIONS

2019 World Congress Eye and Chip Speaker Abstracts, pp. 20-54, 2019.

Gall et al.; Alternating Current Stimulation for Vision Restoration after Optic Nerve Damage: A Randomized Clinical Trial, PLOS One, pp. 1-13, 2016, accessed Nov. 12, 2018.

Chow et al.; "The Artificial Silicon Retina in Retinitis Pigmentosa Patients", Trans Am Ophthalmol Soc., vol. 108, pp. 120-154, 2010.

Dawson et al.; "Improved Electrode for Electroretinography," Invest. Ophthalmol. Visual Sci. vol. 8, No. 9, pp. 988-991, Sep. 1979, accessed on May 2, 2019.

Diagnosys DTL Brochure, Diagnosys, LLC, 2016, Accessed Nov. 20, 2017.

DTL Installation, Diagnosys LLC, Accessed Oct. 6, 2020.

Bittner et al.; "Longevity of Visual Improvements following Transcorneal Electrical Stimulation and Efficacy of Retreatment in Three Individuals with Retinitis Pigmentosa", Graefe's Archive for Clinical and Experimental Ophthalmology, 2017, Published online on Dec. 8, 2017.

H110002B Summary of Safety and Probable Benefits, Second Sight Medical Products Inc., issued Dec. 11, 2001.

H110002C Second Sight Manuals, Second Sight Medical Products Inc., 2013.

Naycheva et al.; Phosphene Thresholds Elicited by Trasncorneal Electrical Stimulation in Healthy Subjects and Patients with Retinal Disease, Investigative Ophthamology and Visual Science, vol. 53, No. 12, pp. 7440-7448, 2012, accessed on Sep. 20, 2018.

Schatz et al.; "Transcorneal Electrical Stimulation for Patients with Retinitis Pigmentosa: A Prospective Randomized, Sham-Controlled Follow-Up Study Over 1 Year", Investigative Ophthalmology and Visual Science, vol. 58, No. 1, pp. 257-269, 2017. Accessed on Sep. 25, 2018.

Scyfix SF700 Manual, Instructions for Use, pp. 1-28, Scyfix LLC. 2023. (No. Year Given).

Stauffer et al.; "Skin Conformal Polymer Electrodes for Clinical ECG and EEG Recordings," Advanced Healthcare Materials pp. 1-10, 2018.

Manthey et al.; "Using Electrical Stimulation to Enhance the Efficacy of Cell Transplantation Therapies for Neurodegenerative Retinal Diseases: Concepts, Challenges, and Future Perspectives", Cell Transplantation, vol. 26, pp. 949-965, 2017.

Invitation To Pay Additional Fees dated Dec. 17, 2019 for International Application No. PCT/US2019/054028.

Invitation To Pay Additional Fees dated Feb. 14, 2020 for International Application No. PCT/US2019/063580.

International Search Report and Written Opinion dated Jul. 10, 2020 for International Application No. PCT/US2020/027438.

Krakova et al., "Spatial Differences in Corneal Electroretinogram Potentials Measured in Rat with a Contact Lens Electrode Array," Doc Ophthalmol vol. 129, pp. 151-166, 2014.

U.S. Application No. 17,782, 100 filed Jun. 21, 2022.

\* cited by examiner

OCULAR THERAPY MODES AND SYSTEMS

CROSS REFERENCE TO RELATED APPLICATIONS

The present application is a national stage application of PCT Application No PCT/US2020/041166, filed Jul. 8, 2020, which claims the benefit of and priority to U.S. Provisional Patent Application Ser. No. 62/873,450, filed Jul. 12, 2019, titled OCULAR THERAPY MODES AND SYSTEMS, the disclosure of which is incorporated herein by reference.

FIELD

The present invention relates generally to the delivery of therapeutic energy for treatment of a variety of conditions. More particularly, the present invention is directed to systems and methods adapted to deliver energy to the eye and/or tissue around the eye.

BACKGROUND

Therapy to prevent, stop or slow the progression of, or to reverse diseases of the eye is of great interest. As life expectancy expands, more and more of the population is at risk for age related macular degeneration (AMD). Meanwhile, smaller populations of patients suffer from a variety of maladies, including Stargardt's disease, diabetic retinopathy, retinitis pigmentosa, and other degenerative conditions that affect the retina of the eye. A wide variety of other vision disorders exist which can lead to partial or total blindness. There is a continuing demand for new, adjunctive, and/or alternative systems and methods to treat such disorders including by preventing, arresting or reversing disease progress, or at least by alleviating ongoing symptoms.

A variety of proposed head worn apparatuses have been disclosed for the delivery of electrical stimulus (sometimes referred to as microcurrent therapy) to the eye. Patches, goggles, and devices resembling glasses have been proposed. However, there remains a continuing demand for improved head worn apparatuses for delivering therapy to persons afflicted with diseases of the eye, as well as other conditions (headaches, sleep disorders, fatigue) that may be treated by delivering therapy to the eye and/or surrounding tissue.

OVERVIEW

The present inventors have recognized, among other things, that a problem to be solved is the need for new patient interfaces for delivering energy and/or therapy to the eye and surrounding tissues. One form of energy delivery is electrical therapy which, when applied to the eye may be referred to as "ocular modulation." Such therapy may be electrocurrent therapy, microcurrent therapy or millicurrent therapy, without intending to limit the scope of the invention to a particular range of current with such terms. New and alternative approaches to therapy delivery for targets in and around the eye are desired.

A first illustrative and non-limiting example takes the form of an apparatus for treating a condition of the eye comprising a pulse generator coupled to a plurality of electrodes, the pulse generator comprising circuitry including a controller configured to perform a method of treating an eye condition by delivery of therapy between at least first and second electrodes.

Additionally or alternatively, the apparatus may further comprise a headband that holds the pulse generator. In another alternative, the headband further holds the first and second electrodes in desired positions on the forehead of the patient. Additionally or alternatively, the apparatus may further comprise an earpiece adapted to couple onto the ear of the patient, the pulse generator being carried by the earpiece. Additionally or alternatively, the apparatus may further comprise an armband adapted to be carried on an arm of the patient, the pulse generator being carried by the armband. Additionally or alternatively, the apparatus may further comprise a neckpiece adapted to be worn on the neck of the patient, the pulse generator being carried by the neckpiece. Additionally or alternatively, the apparatus may further comprise a frame having an earpiece and a noserest, the pulse generator being carried by the frame. Additionally or alternatively, the apparatus may further comprise a harness wearable on the torso of the patient, pulse generator being carried by the harness.

Additionally or alternatively, the apparatus may further comprise a third electrode, wherein the controller is further configured to deliver therapy in a spatial pattern using the first second and third electrodes to issue therapy with at least first and second steps, wherein utilization of the first, second and third electrodes varies from the first to the second step. Additionally or alternatively, the utilization varies as follows: in the first stage, first total current is issued by the first and second electrodes to the third electrode, with the first electrode issuing a first percentage of the first total current and the second electrode issuing a second percentage of the first total current; and in the second stage, second total current is issued by the first and second electrodes to the third electrode, with the first electrode issuing a third percentage of the second total current and the second electrode issuing a fourth percentage of the second total current.

Additionally or alternatively, the apparatus may further comprise third and fourth electrodes, wherein the first and second electrodes are configured for placement on the left and right eyelids, respectively, and the third and fourth electrodes are configured for placement behind the left and right ears, respectively, and the controller is configured to deliver therapy in a spatially varying pattern using the first, second, third and fourth electrodes in at least first and second stages, wherein utilization of the first, second, third and fourth electrodes varies from the first stage to the second stage. Additionally or alternatively, the utilization varies as follows: in the first stage, a first total current is issued by the first and second electrodes to the third and fourth electrodes, with the first electrode issuing a first percentage of the first total current, the second electrode issuing a second percentage of the first total current, the third electrode receiving a third percentage of the first total current, and the fourth electrode receiving a fourth percentage of the first total current; and in the second stage, a second total current is issued by the first and second electrodes to the third and fourth electrodes, with the first electrode issuing a fifth percentage of the second total current, the second electrode issuing a sixth percentage of the second total current, the third electrode receiving a seventh percentage of the second total current, and the fourth electrode receiving an eighth percentage of the second total current.

Additionally or alternatively, the controller is configured such that the first and second total currents are not equal to one another.

Further variants on the above, as well as additional illustrative examples in both apparatus and method form are described in further detail below.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
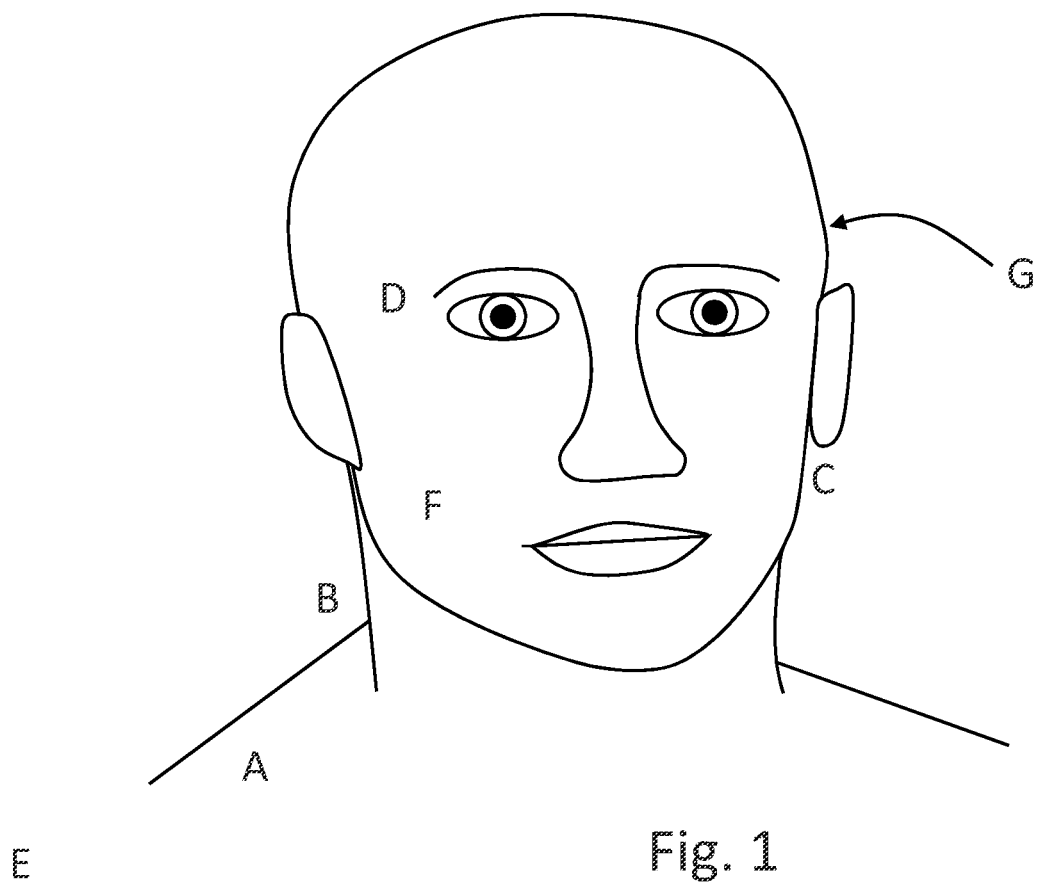
FIGS. 1-2 shows select anatomy of the human eye and face.

The present invention is generally directed to systems for delivering stimulus to the eye of a patient or user. Some patients may have a disease of the eye, such as one or more of the following: dry or wet macular degeneration, inherited retinal disease, presbyopia, diabetic retinopathy, glaucoma, retinitis pigmentosa, Stargardt's, CMV-retinitis, Best's disease, macular dystrophy, optic neuritis, ischemic anterior optic neuritis, Usher's syndrome, Leber's congenital amaurosis, cone-rod dystrophy, cone dystrophy, choroideremia and gyrate atrophy, central retinal artery occlusion, central retinal vein occlusion, branch retinal artery occlusion, branch retinal vein occlusion, central serous chorioretinopathy, cystoid macular edema, ocular histoplasmosis, ocular toxoplasmosis, retinopathy of prematurity, amblyopia, strabismus, and nystagmus. Some patients suffer from traumatic injuries (such as optic nerve crush), or from vascular insufficiencies that can also negatively affect vision. Other patients may have different conditions that may be treatable by delivery of therapeutic energy to the eye and tissue near the eye. In addition or alternative to vision disorders, some illustrative conditions may include dry eye, headaches, migraine headaches, sleep disorders, fatigue, difficulty focusing or concentrating, problems with blinking, undesired movements (tics or twitching, for example). In some examples, a preventative therapy may be provided for persons who have not been diagnosed with a condition but who may be predisposed for such conditions, such as for patients with genetic markers, family history, or other medical conditions such as diabetes that increase the risk of vision disorders.

In some examples, new systems and methods for delivering electrical stimulus to a user may be used as a stand-alone therapy or may be combined with other stimuli or therapy, such as light stimulus and/or the provision of cellular, biological, and/or pharmaceutical agents, for therapeutic or preventive reasons. Some examples are suitable for use in ocular modulation.

As used herein, "ocular modulation" includes the application to the eye of an electrical signal, delivered non-invasively, or minimally-invasively, to achieve a therapeutic benefit. Therapeutic benefit may include, for example and without limitation, improving or altering blood flow, upregulating or downregulating synthesis, degradation, binding, release or activity of proteins, enzymes, DNA, RNA, polysaccharides or other endogenous physiological or pathological biomolecules; and/or upregulating, downregulating, activating, deactivating physiological or pathological biopathways, etc. Ocular modulation may be combined with the administration of pharmaceuticals, exogenously derived biomolecules, cell therapy, or photo-, electro- or magneto-reactive or active particles, such as nanoparticles, before, during or after an electrical signal is applied.

In some examples, the devices and systems disclosed herein are suited for use in conjunction with exogenous and/or endogenous stem cell transplantation therapies. For example, a method may comprise delivery of electrical stimulation before, during, or after stem cell transplantation to improve cell survival, repair and/or replacement. In illustrations, the use of methods and systems disclosed herein may enhance native cell survival, transplanted cell survival, transplanted cell integration, and functional synapse formation and/or axon regeneration. Non-limiting examples of endogenous stem cell types which may be suitable for transplantation in combination with systems or devices of the present invention include Müller cells, retinal pigment epithelial cells (RPE cells) and ciliary pigmented epithelial cells (CPE). Non-limiting examples of exogenous stem cells suitable for transplantation according to some embodiments of the invention include neural stem cells (NSCs), mesenchymal stem cells (MSCs) derived from bone marrow, adipose tissue or dental pulp and stem cells from the inner cell mass of the blastocyst and induced pluripotent stem cells (iPSCs). See, for example, "Using Electrical Stimulation to Enhance the Efficacy of Cell Transplantation Therapies for Neurodegenerative Retinal Diseases: Concepts, Challenges, and Future Perspectives", Abby Leigh Manthey, et al., Cell Transplantation, Vol. 26, pp. 949-965, 2017.

In some examples, combination of therapy systems of the invention with biological or pharmaceutical agents may provide improved efficacy or reduced side effects associated with such biological or pharmaceutical agents when administered alone. Pharmaceutical agents currently used to reduce the growth of new blood vessels in wet AMD include anti-angiogenics such Bevacizumab (Avastin®), Ranibizumab (Lucentis®) and Aflibercept (Eylea®), etc. While the benefit of these agents for mitigating symptoms associated with wet AMD are well-known, these agents also may have side effects including increased eye pressure, inflammation of the eye and others. A benefit of systems disclosed herein includes modulation of cytokines and other endogenous inflammatory factors involved in the inflammation process. In some embodiments it is foreseen that administration of anti-angiogenic agents listed above or other pharmaceuticals in combination with electrical therapy applied simultaneously with, before (e.g. 1, 2, 12, 24, 36, 48 and/or 96 hours before), or after (e.g. 1, 2, 12, 24, 36, 48 and/or 96 hours after), injection of such anti-angiogenics, at stimulation parameters used herein, may beneficially improve the efficacy and/or reduce the likelihood of side effects associated with administration of such agents.

Several different modes of energy delivery can be used including mechanical delivery (such as sonic energy, including for example, ultrasound), light-based delivery (such as by the delivery of collimated or non-collimated light of selected wavelengths, for example using a laser, a light emitting diode, etc.), electrical delivery (such as by the delivery of an electrical signal), and/or magnetic delivery (such as by generating a magnetic field or fields). In some examples, one mode of therapy delivery is used, while the same or a different mode is used to monitor therapy delivery. One component of several examples is the use of configurations that are adapted to provide enhanced tissue contact, enhanced therapy delivery, improved efficiency of energy delivery, targeted therapy locations, improved user comfort and/or compliance, and/or reduced likelihood of tissue injury or irritation.

Various features for delivering therapy may be understood by review of, for example and without intending limitation, U.S. Pat. No. 7,251,528 to Harold, US PG Pat. Pub. No. 2020/0101290, titled SYSTEM AND METHODS FOR CONTROLLED ELECTRICAL MODULATION FOR VISION THERAPY, US PG Pat. Pub. No. 2020/0171307, titled HEAD WORN APPARATUSES FOR VISION THERAPY, U.S. patent application Ser. No. 16/844,421, filed Apr. 9, 2020, titled SYSTEMS AND INTERFACES FOR OCULAR THERAPY, U.S. patent application Ser. No. 16/900,115, filed Jun. 12, 2020, titled, WEARABLE MEDICAL DEVICE, and PCT Application No. PCT/US20/39776, filed on Jun. 26, 2020, titled SYSTEMS AND INTERFACES FOR OCULAR THERAPY, the disclosures of which are incorporated herein by reference as showing waveforms, structures, apparatuses and systems for delivery of ocular modulation.

FIG. 1 illustrates the head, neck and upper torso of a patient, with several indicators for placement of an electrode that may be used in the delivery of ocular therapy. The positions shown in FIG. 1 may be useful for placement of an electrode for purposes of therapy delivery. A variety of cutaneous positions are shown as well as at least one body-internal position. The illustrated positions are:

A—on the torso, which includes the shoulder, back and chest of the patient.
B—on the neck, which may include placement at or off of midline on the anterior or, more preferably, posterior neck; the lateral sides of the neck may be used instead if desired.
C—on or behind the ear of the patient.
D—near the temple of the patient.
E—on an extremity of a patient, including, without limitation, the arms, legs, elbow, wrist, hand or foot.
F—over the mandible on the right or left side of the face.
G—on the back of the head, which may include near the base of the skull or superior thereto.

An electrode may be provided on a skin patch, which may include an adhesive to hold the skin patch in place. The electrode may be a dry electrode or a wet electrode. Dry electrodes can be bare metal, coated metal, or conductive polymers. Some examples of dry electrodes may comprise a flexible material, such as a polymer, fabric, a silicon wafer, etc. on which a metallization layer (silver, gold, platinum, copper, nickel, etc.) is deposited, such as by simple spraying or using any of a variety of microfabrication deposition techniques (for example, sputtering). A variety of dry electrode concepts are described by Chlaihawia et al., *Development of Printed and Flexible dry ECG electrodes*, in Sensing and Bio-Sensing Research 20 (2018) 9-15. Wet electrodes may start with similar materials, but are coated with an electrolytic, conductive gel prior to placement. A wettable or liquid carrying electrode may be used as well, by, for example, soaking a cellulose or cotton material in saline or other electrolyte.

Figure 2:
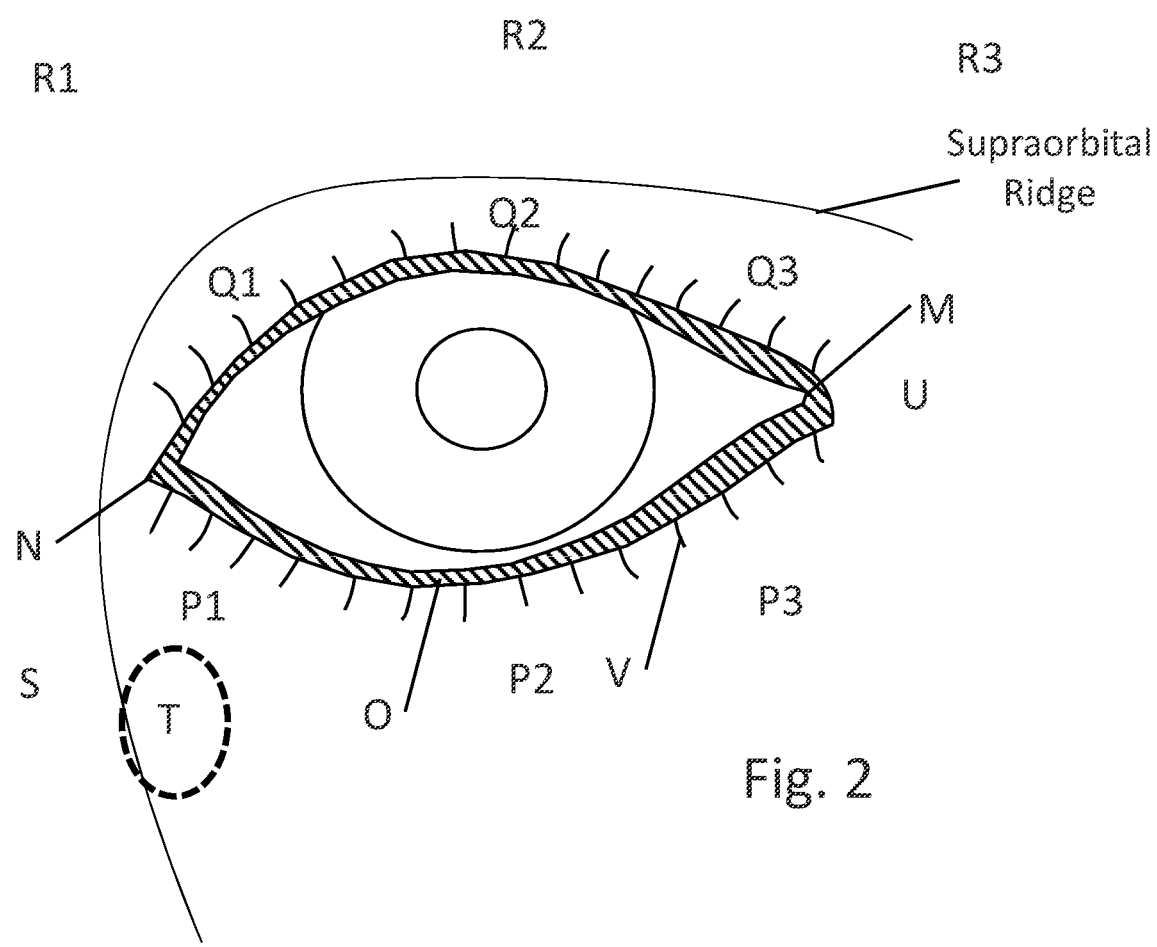

FIG. 2 illustrates the eye of a patient, with various electrode positions highlighted:

M—the lateral canthus
N—the medial canthus, or on the lacrimal puncta, whether superior or inferior
O—the inferior or superior conjunctiva
P1, P2, P3—the inferior eyelid, including medial P1, central P2 and lateral P3 positions relative to the eye
Q1, Q2, Q3—the superior eyelid, including medial Q1, central Q2 and lateral Q3 positions relative to the eye
R1, R2, R3—the forehead, which may include a medial R1, central R2 and lateral R3 positions relative to the eye; the medial position R1 may be, for example, at or near midline and/or directly over the nose, and each of R1, R2, R3 may be defined superior to the supraorbital ridge such as, for example, in the space between the eyebrows and the hairline, or in a range of about 0.1 to about 3 cm, to about 5 cm, superior to the supraorbital ridge
S—on the side of the nose, which may also be described a medial to the medial canthus
T—below the skin in an anatomical opening, cavity or lumen, such as in the nasal cavity or in the nasolacrimal duct
U—lateral to the lateral canthus, including over the zygomatic bone
V—In contact with the conjunctiva and/or upper/superior or lower/inferior eyelid by its inclusion on an apparatus that attaches to the eyelashes.

For bipolar uses, any pair of positions M-V just described may be used as a therapy or diagnostic vector. An indifferent electrode may, optionally, be used or omitted when a bipolar therapy or diagnostic vector is defined; if used, an indifferent electrode may be placed elsewhere on the patient such as any of positions A-G. For monopolar uses, any combination of one or more of positions M-V just described may be paired with one or more electrodes from the above list A-G and used as a therapy or diagnostic vector. Therapy outputs may be monophasic, or multiphasic (biphasic or triphasic, for example). For purposes herein, therapy delivered between an electrode in a first position on the right side of the patient's face or head, and an electrode in a second position on the left side of the patient's face or head, will be described as a bipolar therapy or diagnostic vector. Any pairing of an electrode in any of positions M-V on the right side of the patient's face or head with an electrode in any of positions M-V on the left side of the patient's face or head may be used as a therapy or diagnostic vector.

As used herein, a therapy vector is an electrical vector used to deliver electrical energy, whether current controlled or voltage controlled, using at least one anode and one cathode (for multiphasic therapies, the anode and cathode are named according to their use during the first phase of an output). A diagnostic vector is an electrical vector used for sensing an endogenous signal or sensing a response to an input signal between two electrodes. An endogenous signal may be, for example, a myopotential generated by a muscle or a signal generated by operation of a neural action potential, while a sensed response may be, for example, an impedance encountered by an output signal or an electrical field sensed at an electrode which is not used for outputting a signal. In some cases both endogenous and response signals may be sensed, such as when an issued therapy signal is sensed along with an action potential responsive to the therapy signal. Additional signals, such as magnetic, optic, or mechanical signals may also be delivered to a patient, and/or sensed by a system. Further, an electrical or other therapy may be combined with infusion of a drug (such as an angiogenic or anti-angiogenic drug) or biological product (such as stem cells).

As used herein, the conjunctiva will generally refer to the palpebral conjunctiva that cover the back side of the eyelids.

The palpebral conjunctiva is shown in an exaggerated form throughout the figures of the present application. Further, as used herein, medial canthus placement may involve placement of an electrode in contact with one or more of the conjunctiva, the plica semilunaris and the lacrimal caruncle.

The system for delivering therapy and/or measuring diagnostics typically includes a pulse generator. In various embodiments, a pulse generator may be integrated into a wearable product, such as a hat, visor, headband, glasses-type frame, goggle, earpiece, neck worn apparatus, or a canister, box or other housing worn on the patient's torso or elsewhere, such as on a belt worn at the waistline or on an arm cuff.

A pulse generator may include a power source, such as a rechargeable or non-rechargeable battery. A pulse generator may include an application specific integrated circuit (ASIC) having control circuitry, memory, and various operational circuits such as current or voltage sources, operational amplifiers, filtering circuitry, etc. as the skilled artisan will recognize may be used to control device operation. For example, the pulse generator may comprise circuitry defining a state machine, or may include a microprocessor or microcontroller, which may or may not be part of an ASIC. The processor, by itself or by the use of stored instruction sets in a machine readable medium, such as a memory circuit, may be configured for analysis of sensed biological signals or biological response to input signals (or other events), diagnosis of device or patient related conditions, control of device functionality (including therapy output, communication, data management/storage, sensing, etc.), delivery of therapy or outputting of signals used for diagnostic purposes, or any other function of the device.

Memory circuitry, such as Flash memory or any other suitable memory type, which may include volatile and/or non-volatile memory, may be used to store instructions in a non-transitory medium for analytic, diagnostic, therapeutic purposes as well as communications, system control and data management. Input/output (I/O) circuitry may be provided using, for example, inputs and outputs of a microcontroller, a signal processing and/or amplifier chip, or using discrete components, or any other suitable structure. For example, a multiple-output system may include a plurality of current or voltage controlled output circuits, such as a plurality of current mirrors or amplifiers, which may be controlled in some examples by a microcontroller. Analog-to-digital conversion circuitry may be used to aid in sensing and diagnostic functions, and digital-to-analog conversion circuits may be used for issuing stimuli for therapy or diagnostic functions. I/O circuitry may comprise known filtering, buffering or protective circuits such as DC blocking capacitors.

A communications block may be included using, for example a MedRadio telemetry circuit, an inductive telemetry circuit, or a Bluetooth™ circuit, such as a Bluetooth™ Low Energy (BLE) circuit. A communication block may thus include an antenna and related circuitry (such as a crystal or other oscillator) for performing telemetry; other communication modes (optic, sonic) may be used instead if desired. A separate programmer or remote control may be provided to allow a clinician or user/patient to activate, deactivate, program or change therapy or diagnostic functions. The programmer or remote control may be a dedicated device or may be a multiuse device, such as a smartphone or tablet computer. For example, internal circuitry in a smartphone, tablet, laptop, or desktop computer may include a Bluetooth communication circuit usable with a communications block of a pulse generator. In another example, a dongle may be used to plug into a port on a smartphone, tablet, laptop, or desktop computer, with the dongle having therein a dedicated communication circuit such as a Medradio circuit operable in the 401-406 MHz range.

Systems as described herein may be adapted to communicate and/or cooperate with additional diagnostic or therapeutic systems, such as, for example, monitoring or therapy devices for neurological and cardiac purposes, diabetes management, etc. For example, a system may communicate with a blood pressure monitoring apparatus to obtain blood pressure measurements during therapy delivery, or it may communicate with a cardiac sensing device to indicate when therapy outputs (possibly causing interference) are being generated. In another example, a device may communicate with a vagus nerve stimulation device or system to obtain information indicating the sympathetic tone before, during and/or after therapy delivery. If the sympathetic tone is not changed during therapy it may be that the therapy has not caused activation of cells in the target tissue, for example, potentially indicating a need to change therapy parameters such as an increase or decrease in one or more of the amplitude, frequency, duty cycle, pulse width, or other parameter, or a change in or repositioning of electrodes used to define a therapy vector.

Some particular examples are illustrated in FIGS. 3-13 below. This series of examples is purely for illustrative purposes, and the selected configurations shown are not necessarily preferred relative to other examples described herein.

Figure 3:
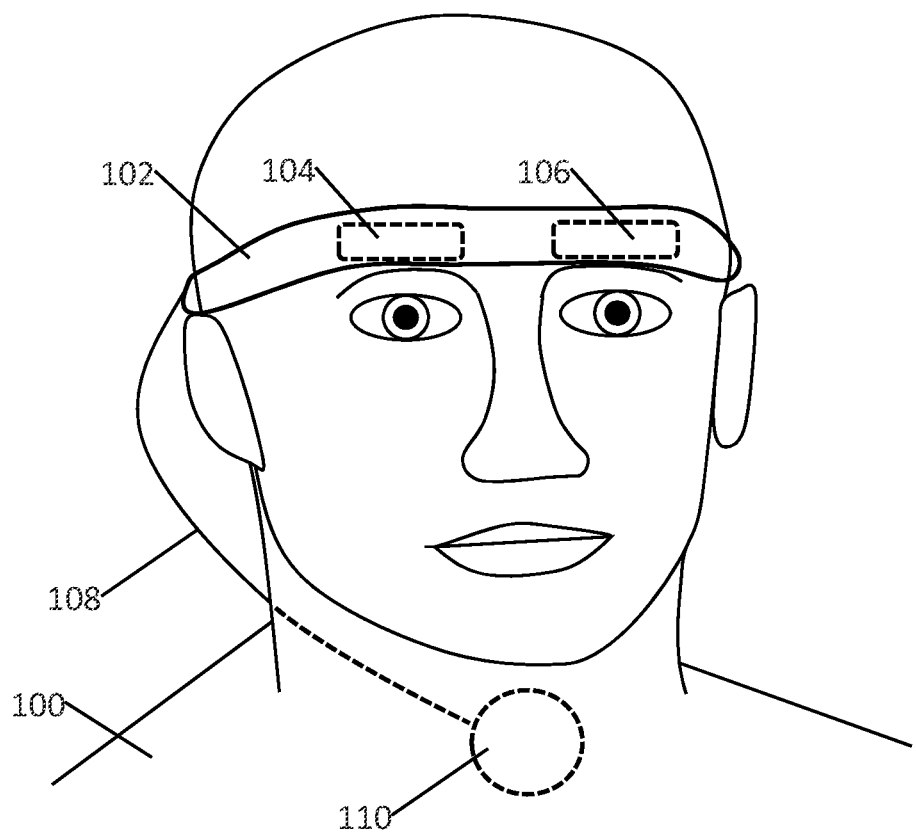
FIGS. 3-13 show ocular therapy apparatuses in use configurations.

FIG. 3 shows an ocular therapy apparatus in a use configuration on a patient 100. The system as shown comprises a headband 102 that holds electrodes 104, 106 on the patient's 100 forehead, more or less directly over each eye. A lead 108 extends to a remote electrode 110 that can be placed on the back or side of the patient's neck, or if desired, on the upper torso or on the back of the head. In some examples, the remote electrode 110 could instead by carried by the headband 102 and positioned against the back of the patient's head, behind the ear, or on the temple. The pulse generator for the system may be carried by the headband, making for a simple and relatively easy to use product. The headband 102 may be elastic or may comprise a resilient or elastic internal element to hold it in place on the patient's 100 head. The electrodes 104, 106, 110 may be dry, metal, gel covered, or wettable electrodes. More than one electrode type may be used; for example, electrodes 104, 106 may be dry electrodes held against the patient's forehead by the headband, while electrode 110 may be a gel electrode held in place on the neck of the patient by a semi-adhesive gel element that is placed on the electrode 110 and then discarded after use. Other combinations of different electrode types may be used. Stimuli may be delivered in various potential vectors, such as:

Between electrodes 104 and 106;
    Between electrodes 104 and 110 or 106 and 110;
    Between a common pole of any two of 104, 106, 110 and the remaining electrode;
    Simultaneously between electrodes 104 and 110, and between 106 and 110, such as by having two separate current sources for electrodes 104, 106;
    Alternating between 104 and 110 and then 106 and 110 in a series of stimuli.

Each such vector may be used for therapy or diagnostic purposes. Different combinations may be used for different purposes, such as by having the two forehead mounted electrodes deliver a therapy targeting an anterior structure in the eye in a bipolar configuration, and pairing electrode 110 with either or both of the forehead electrodes 104, 106 to target a deeper structure in the eye such as the retina, maculae, or optic nerve.

Other forehead positions may be used in place of those shown, which are generally directly superior to each eye, such as by having an electrode at midline, and/or by having electrodes superior to the medial or lateral edges of the eye. Electrodes for forehead placement may be, for example, at or just above the supraorbital ridge, below the hairline, superior to the eyebrow, or 0.1 to 5 cm superior to the supraorbital ridge, such as at 0.5, 1, 1.5, 2, 2.5, 3, 3.5, 4, 4.5 or 5 cm superior to the supraorbital ridge.

Figure 4:
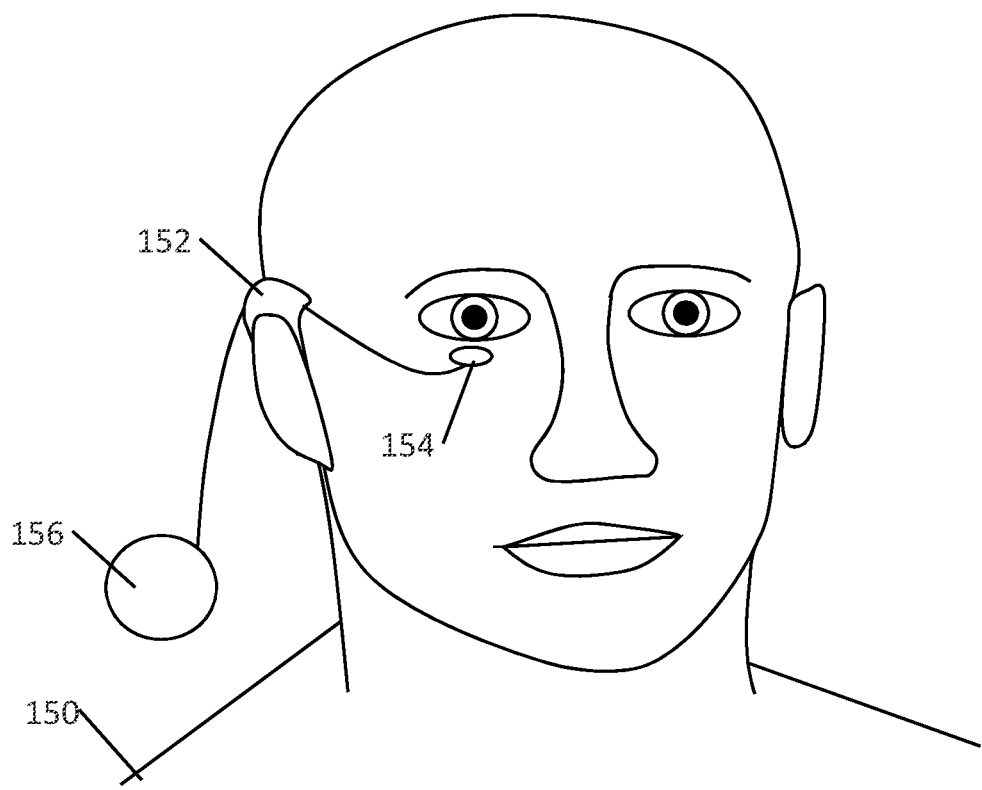

FIG. 4 shows an ocular therapy apparatus in a use configuration on a patient 150. The system comprises a pulse generator 152 designed as an earpiece that wraps around the back of the ear, similar to a behind-the-ear hearing aid. The pulse generator 152 is coupled by a wire to a first electrode 154 that is placed on the inferior eyelid of the patient 150, as well as by another wire to a remote electrode 156 which may be placed elsewhere on the patient, such as on the back of the head or neck, or on the torso, on a limb, or on the temple or in the mandible, as desired. The housing of the pulse generator 152 may include one or more electrodes on a skin-facing surface thereof, if desired, to replace the remote electrode 156 or to be used in combination with the eyelid electrode 154 and remote electrode 156 to provide a plurality of vectors for therapy or diagnostic purposes.

Figure 5:
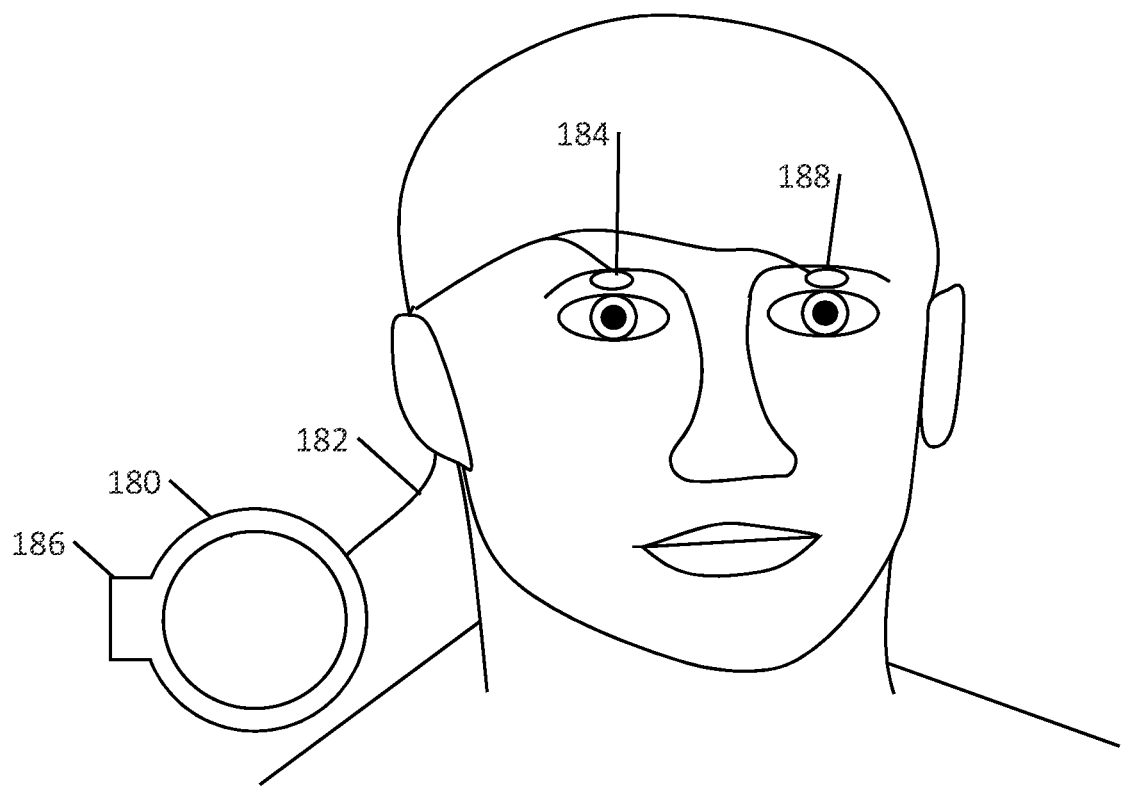

FIG. 5 shows an ocular therapy apparatus in a use configuration on a patient. Here, a remote electrode is on a cuff 180 that may be worn on the arm. A wire 182 connects a facial electrode 184, shown here on the superior eyelid, and rests on the patient's ear for support, similar to a wireless microphone that is held on the user's ear. The cuff 180 may carry or have integrated therein the pulse generator circuitry 186. In some examples, a second facial electrode 188 is provided as well, facilitating therapy for both the right and left eyes. While several examples shown in the figures illustrate electrodes on only one eye or on only one side of the face or head, it should be understood that both eyes or sides of the face or head may have electrodes thereon, allowing treatment and/or diagnostic activities on each eye at the same time and/or to enhance therapy on a given target.

Figure 6:
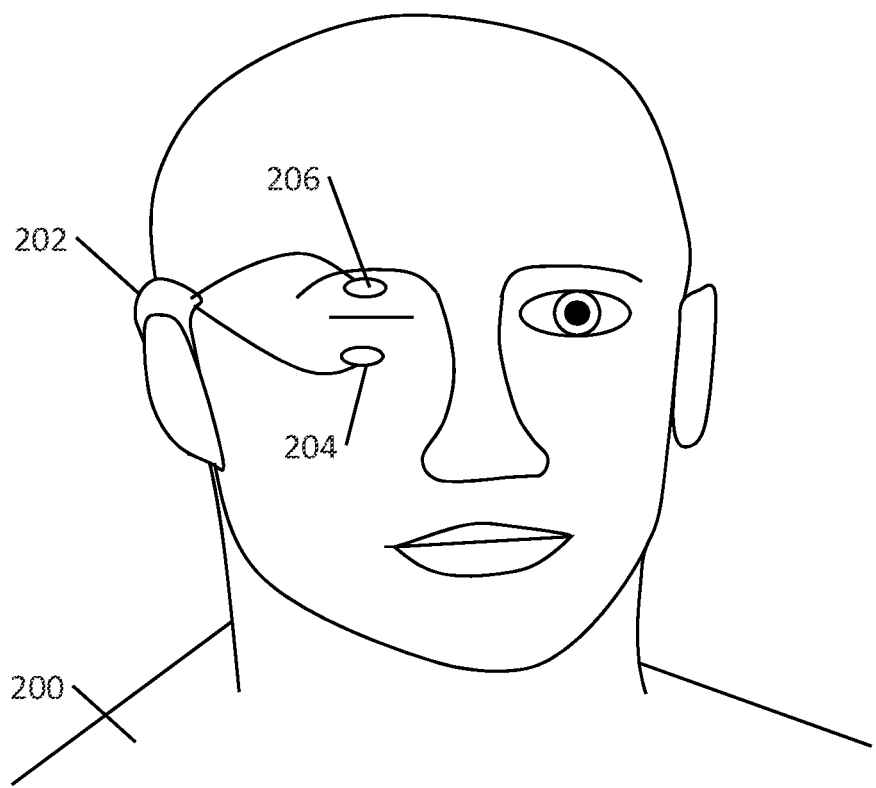

FIG. 6 shows an ocular therapy apparatus in a use configuration on a patient 200. Here the system comprises a pulse generator 202 that is again shown in a behind-the-ear configuration and location, with inferior and superior electrodes 204, 206 on the eye of the patient. A remote electrode may be omitted in some examples, as shown by FIG. 6 though also applicable to the other examples shown in other figures herein. Alternatively, a remote electrode may be attached via wire to the pulse generator 202 or may be provided on an external surface of the pulse generator 202. With superior and inferior eyelid electrodes 204, 206, the patient 200 may need to close the eye being treated during therapy, as shown, though this is not necessarily required. Rather than separately wired electrodes 204, 206, a single eyepiece may be provided having two or more electrodes thereon, such as shown below in FIGS. 10-11 and/or as disclosed in U.S. patent application Ser. No. 16/844,421, titled SYSTEMS AND INTERFACES FOR OCULAR THERAPY, the disclosure of which is incorporated herein by reference.

Figure 7:
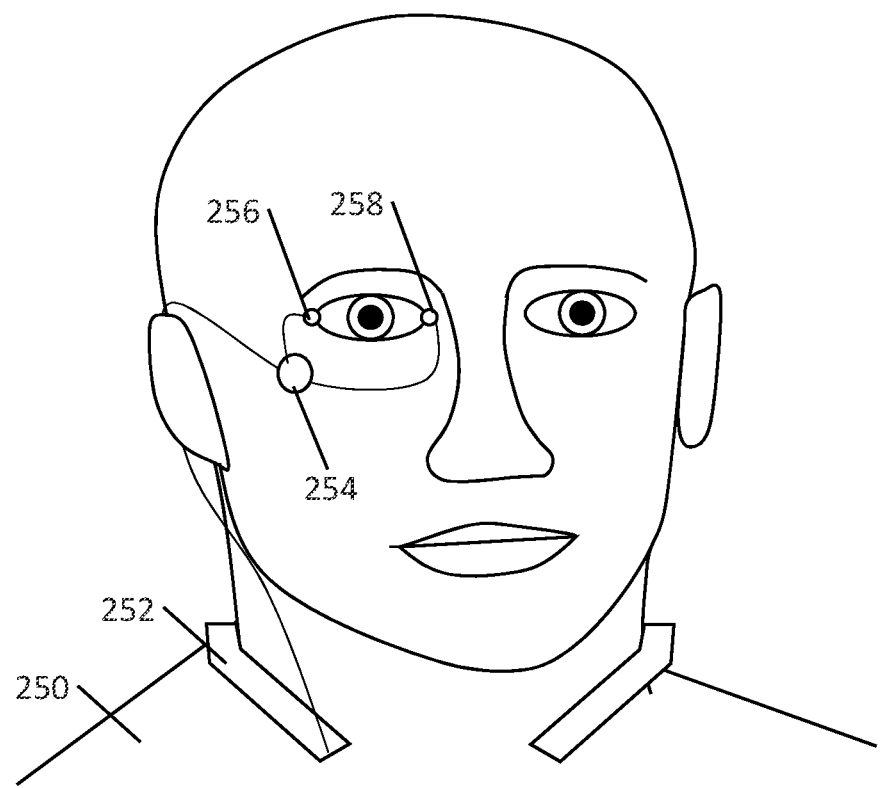

FIG. 7 shows an ocular therapy apparatus in a use configuration on a patient 250. Here a pulse generator 252 is a neck-worn apparatus, more or less in U-shape, as described in U.S. patent application Ser. No. 16/697,689, titled HEAD WORN APPARATUSES FOR VISION THERAPY, and Ser. No. 16/900,115, titled WEARABLE MEDICAL DEVICE, the disclosures of which are incorporated herein by reference. A wire (shown optionally as draped over the ear) connects the pulse generator 252 to a skin patch 254, which is adhered to the patient's skin using medical grade cutaneous adhesive, providing a secure position relative to two electrodes 256, 258 that are placed on the lateral and medial canthus.

In any of the examples herein where an element is designed for securing to the patient's skin, rather than using a medical grade cutaneous adhesive or a semi-adhesive gel, a dry solution may be used instead such as by using adhesive microstructures or nanohairs, the design and making of which are described in US Pub. Pat. App. Nos. 20050181170, and/or 20060202355, the disclosures of which are incorporated herein by reference.

In this example, the electrodes 256, 258 may be wettable electrodes, such as having a silk, cotton or cellulose covering on a metal electrode, as described in PCT Application No. PCT/US20/39776, filed on Jun. 26, 2020, and titled SYSTEMS AND INTERFACES FOR OCULAR THERAPY, the disclosure of which is incorporated herein by reference. A separate return electrode is not illustrated, but as described in the Ser. No. 16/697,689 and Ser. No. 16/900,115 US Patent Apps., the housing of the pulse generator 252 may have one or more conductive areas for use as remote or return electrode(s). In other examples, a separate remote electrode may be provided.

Figure 8:
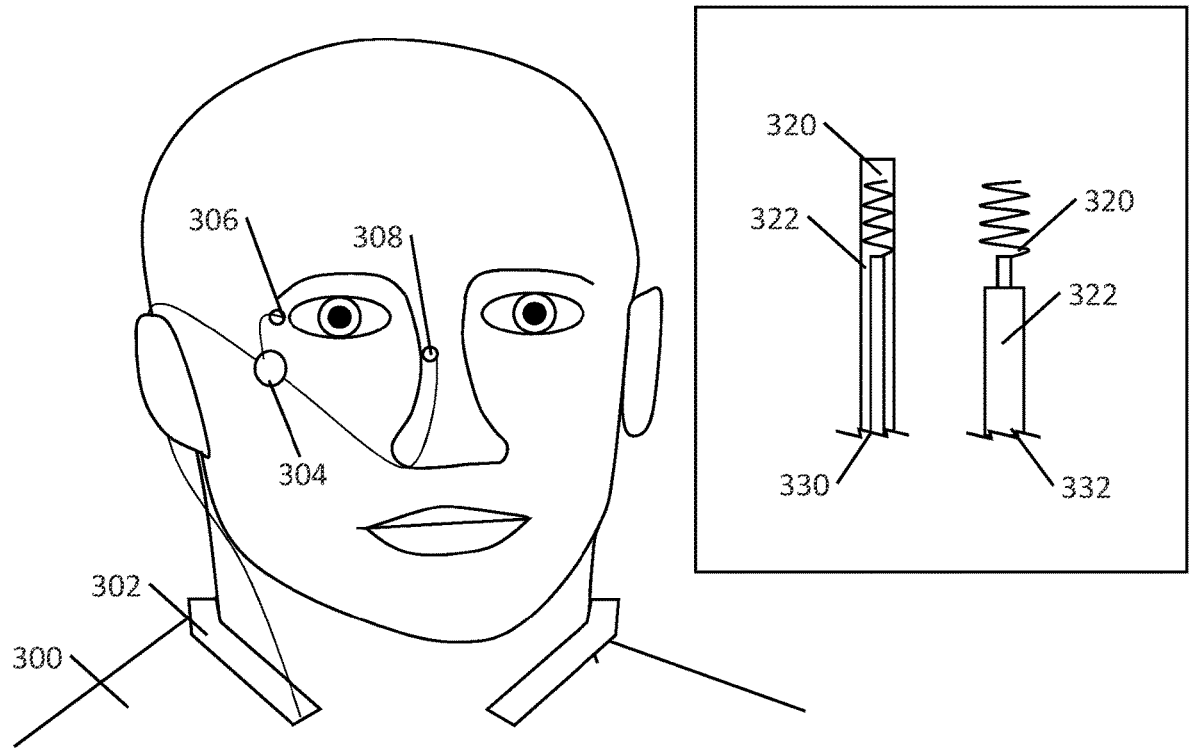

FIG. 8 shows an ocular therapy apparatus in a use configuration on a patient 300. Here, the pulse generator 302 is again a neck-worn apparatus coupled by wire to a skin patch 304 that attaches to an electrode lateral of the eye, rather than being on the canthus, the electrode 306 is placed over the zygomatic bone. A second electrode 308 is shown placed in the sinus cavity of the patient. In some examples, the second electrode 308 may be advanced into a position in the nasolacrimal duct, for example, by the patient so doing, or by a physician. If a physician places electrode 308, it may be on a temporary basis, such as for a single therapy session of a few minutes or hours, or for a short ambulatory period such as a few days, weeks or months, rather than being either permanent or daily placement. In another example, the user may place electrode 308, and the electrode 308 may be a single use product.

While the electrode 308 is shown as a small circle, it may instead take the form of an exposed wire or coil as by, for example, having a coil compressed in a delivery sheath. For example, as shown in the inset, a coil electrode 320 in the form of a helix (or any other coil structure) that is constrained, as shown at 330, inside of a delivery sheath 322 until placed at a desired position, such as by advancement into the nose and into the nasolacrimal duct. As shown at 332, the sheath 322 may be retracted or removed to allow the coil 320 to expand and hold itself in a desired position. For removal, the sheath may be advanced over the coil, or, assuming the coil 320 is used on a temporary basis and does not become attached to the tissue as by a scarring process, the coil 320 and lead may simply be withdrawn. As with other neck worn apparatuses, the pulse generator 302 may carry one or more electrodes on the housing thereof, or may attach by wire to a remote electrode.

In an alternative to emplacing the electrode 308 inside the nose, sinus cavity and/or nasolacrimal duct, the patient 300 may instead wear the electrode 308 on the outside of the nose, such as, for example, on the side of the nose approximately level with the center of the eye. A nasal strip may be used to hold the electrode 308 in position, for example. An electrode may also be placed on the nose by integrating it into the nosepiece of a frame having the general form of an eyeglasses frame.

Figure 9:
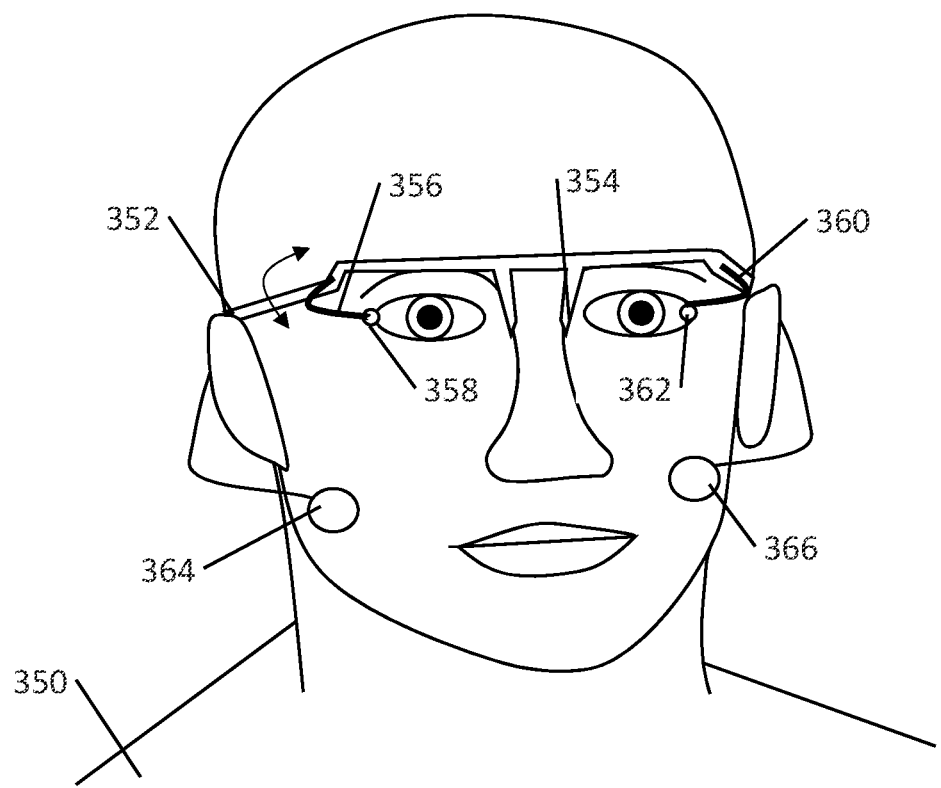

FIG. 9 shows an ocular therapy apparatus in a use configuration on a patient 350. Here the patient is shown wearing a frame 352 similar to those used for eyeglasses, having an earpiece (not shown) and a nose piece 354 to rest on the ears and nose, thus providing a stable frame of reference for applying arms 356, 360 that carry electrodes 358, 362 to positions next to the eye, such as on the lateral canthus as shown in FIG. 9. The arms 356, 358 may pivot and may be shapeable as described in PCT Application No. PCT/US20/39776, filed on Jun. 26, 2020, and titled SYSTEMS AND INTERFACES FOR OCULAR THERAPY, the disclosure of which is incorporated herein by reference. The electrodes 358, 362 may be replaceable and/or wettable electrodes, as described also in the PCT/US20/39776 Patent Application.

Optionally, the system may include one or more mandible electrodes 364, 366, placed generally on the patient's check, such as on the skin over the lateral portions of the mandible. The mandible electrodes 364, 366 may be used as remote or return electrodes relative to the electrodes 358, 362. In one example, therapy may be delivered by crossing the face, as by using an anode/cathode combination of electrode 358 with the mandible electrode 366 on the opposite side of the face. Simultaneously or alternatingly, current may be delivered between the electrode 362 and electrode 366.

In other examples, additional or different electrodes at different locations may be provided using arms placed elsewhere on the frame 352, such as by having one or more arms near the nosepiece 354 to provide an electrode on the medial canthus. The nosepiece 354 may itself carry one or more electrodes thereon to be placed on the nose. Also in other examples, the remote electrodes may be placed elsewhere on the patient 350. The electronics for a system as in FIG. 9 may be integrated into or carried on frame 352.

Figure 10:
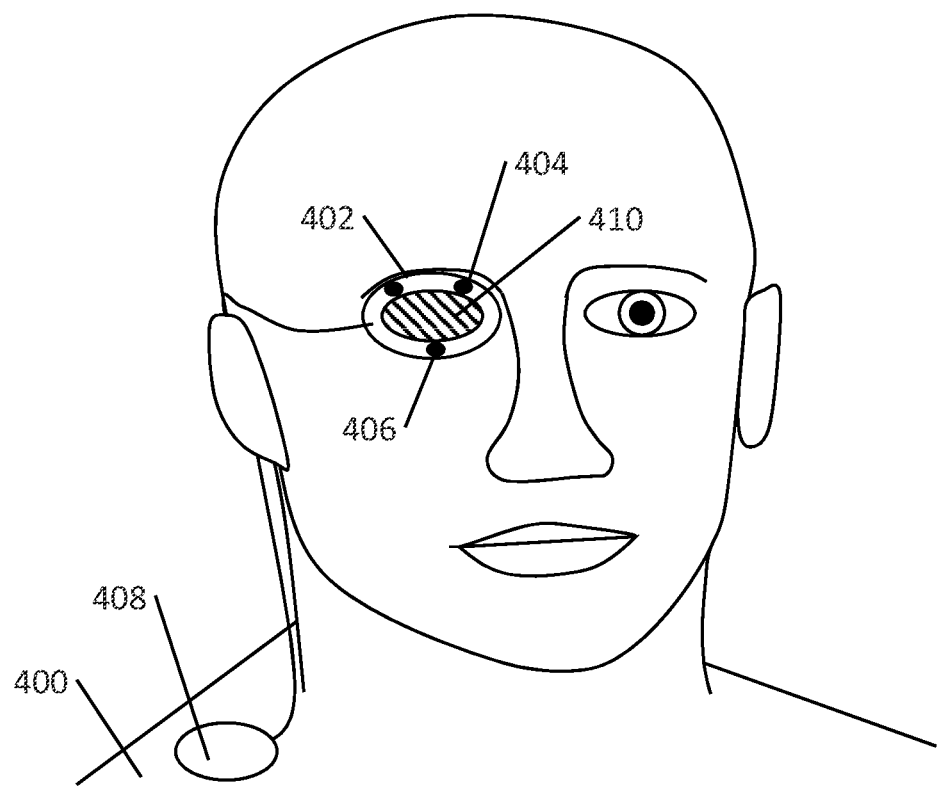

FIG. 10 shows an ocular therapy apparatus in a use configuration on a patient 400. Here, an eyepiece 402 carries a plurality of electrodes 404, 406 at various positions around the patient's eye, creating multiple therapy or diagnostic vectors about the eye itself. A remote electrode 408 may be placed elsewhere on the patient, with a wire connection to the eyepiece 402.

In some examples, the eyepiece 402 may carry electronics for therapy delivery, with or without an internal power source. For example, small, lightweight batteries, such as those used with hearing aids, may be carried on the eyepiece or on the remote electrode 408, or elsewhere on the patient and coupled by wire to the eyepiece, to provide a fully integrated power source. Alternatively, the eyepiece 402 may include a transducer circuit that can receive power through the air, such as by inductive or magnetic transmission, radio or other frequency wireless transmission, or using for example, ultrasound waves. For example, an inductor coupled to a rectifying bridge and capacitor may be provided in the eyepiece (or on the patch associated with the remote electrode 408) to receive magnetic energy generated for example by charger or programmer device. Variants on this example, are provided in U.S. patent application Ser. No. 16/844,421, titled SYSTEMS AND INTERFACES FOR OCULAR THERAPY, the disclosure of which is incorporated herein by reference.

Figure 11:
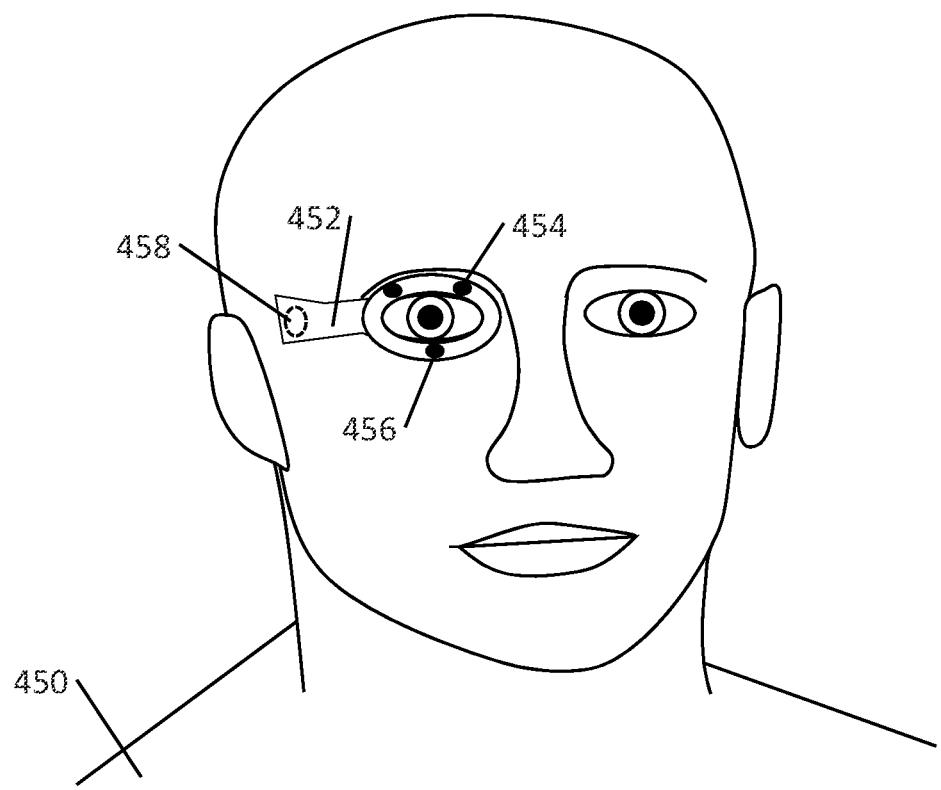

The center 410 of the eyepiece 402 is shown as solid and/or opaque in FIG. 10; it may be open instead as shown in FIG. 11. Whether held in place as shown in FIG. 10, or by a structure existing outside the eye socket (such as a glasses frame as in FIG. 9 or 13, or a structure wrapping to the temple as in FIG. 11, or a structure with a headband or wrap as in FIG. 3), an eye piece 402 having a closed center portion 410 may include features to provide therapy, entertainment, augmented reality, or improved vision. For example, the inner side of the closed portion 410 may form a viewing screen to allow the user to watch a movie, for example, during therapy. In another example, the inner side of the closed portion 410 comprises a screen that is used to display an image useful for therapy or diagnostic purposes, such as a moving dot that the user is instructed to track with his or her vision; as the dot moves, so do the users eyes. The actual motion undertaken may be captured by a camera facing the eye of the closed portion 410, or details of the motion may be sensed by the electrical signals generated as the muscles controlling eye position contract and relax. Such motion can be useful, for example, to determine how much vision distortion/block a person having macular degeneration is experiencing. In another example, eye motion is used to aid in improving the spatial extent of therapy; for example, in some embodiments it may be that the electric fields generated during therapy are inconsistent in relation to the volume of target tissue; by moving the eye, areas of target tissue (such as the retina) move relative to the electric fields, subjecting a greater volume of tissue to higher or different electric field. In another example the closed portion 410 is a corrective lens.

In still another example, the eyepiece, or an associated frame, may include outward facing cameras that capture images, which may in turn be modified and then displayed to the user on a screen on the inside (the palpebral side) of the closed portion 410, using for example, known techniques for warping images as described in U.S. Pat. No. 10,347, 050, creating an augmented reality for the user. In still another example, the inner side of the closed portion 410 may include one or more light sources, such as one or more LED or VCSEL devices that can be used to deliver light therapy into the eye.

FIG. 11 shows an ocular therapy apparatus in a use configuration on a patient 450. Here the patient 450 is wearing an ocular therapy apparatus 452. An eyepiece is included with a plurality of electrodes 454, 456 and a lateral extension of the eyepiece extends around the zygomatic bone to the temple, extending at least partly toward the ear. A remote electrode 458 may be provided at or behind the temple in this example. The electronics may be carried on the lateral extension. In the example shown, the eyepiece perimeter is closed to the shape of an oval, surrounding the entire eye. In other examples, the eyepiece perimeter may be open to form a U-shaped piece.

The lateral extension may carry one or more adhesive patches having medical grade adhesive to hold the apparatus in place, removeably, in the position shown. Such patches may be replaceable elements. Additional designs and details are discussed in U.S. patent application Ser. No. 16/844,421, titled SYSTEMS AND INTERFACES FOR OCULAR THERAPY, the disclosure of which is incorporated herein by reference.

Figure 12:
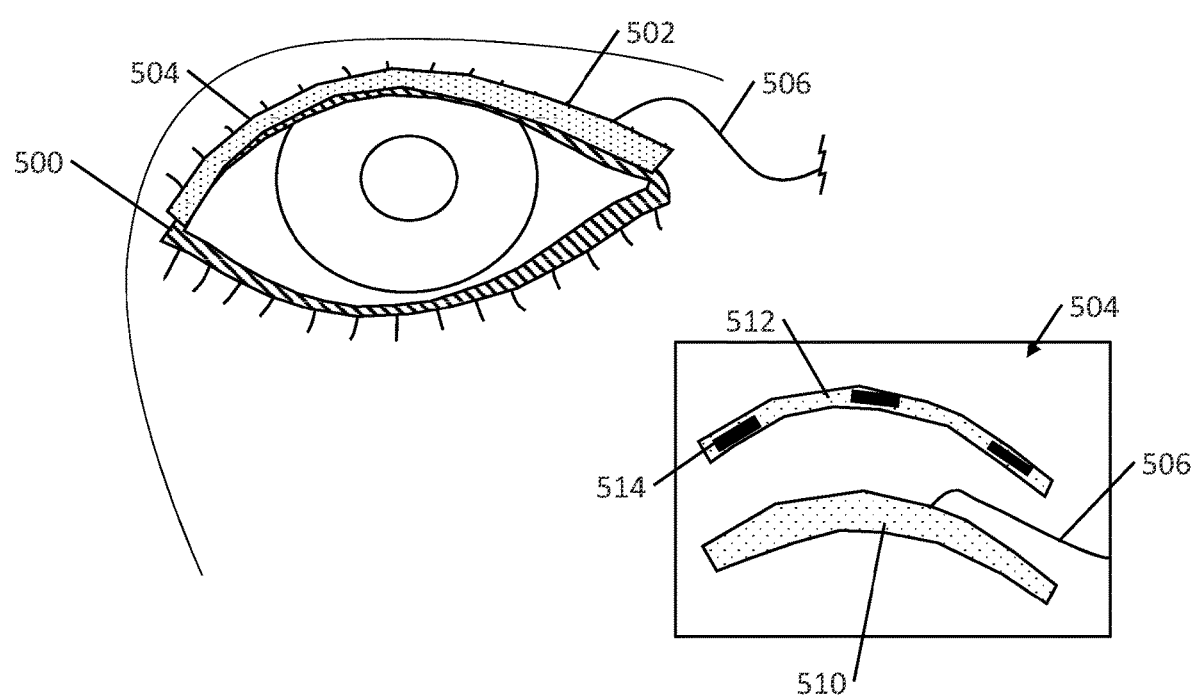

FIG. 12 shows an ocular therapy apparatus in a use configuration on a patient 500. Here, a therapy apparatus 504 is provided to be placed on the conjunctiva by securing, removeably, to the eyelashes 502. False eyelashes are well known in the cosmetics industry and can be simply applied using a magnetic system, such as described in US Pub. Pat. App. Nos. 20090217938 and 20180228237, the disclosures of which are incorporated herein by reference. Example false eyelashes using magnetic attachment are available from One Two Cosmetics and/or Ardell. As applied in FIG. 12, no false eyelash is needed, but a therapy apparatus is provided at 504 that secures to the eyelashes and holds an electrode at the conjunctiva, with a wire connection 506 that may be coupled to a pulse generator such as a pulse generator worn as a glasses-type frame, worn behind the ear, worn on the neck, worn on a headband or hat, or held in a pocket elsewhere on the patient.

As shown in the inset, the therapy apparatus has a first part 510 that includes a conductive element within a wettable electrode material, such as a wicking agent, cellulose, silk or cotton which is provided on a first side of the eyelash, adjacent the conjunctiva. A securing member 512 having one or more magnets 514 is provided on the other side of the eyelash. The first part 510 may include magnets or a ferrous material, such as by using a thin, flexible wire or wires therein to serve as conductive elements within the electrode. In the example of FIG. 12, the therapy apparatus 504 is provided on the superior eyelid; a second such apparatus may be provided as well on the inferior eyelid if desired. The electrode material may, in another example, be a dry electrode or a gel electrode.

Figure 13:
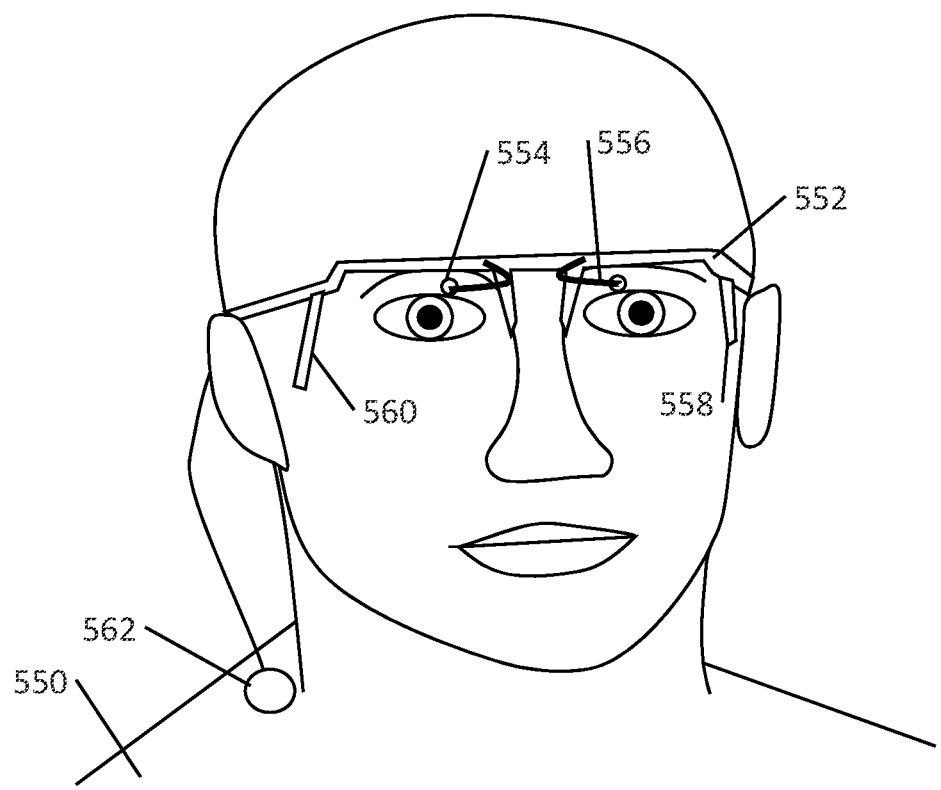

FIG. 13 shows an ocular therapy apparatus in a use configuration on a patient 550. A therapy apparatus 552 is shown generally in the form of an eyeglasses frame, and includes first and second electrodes 554, 556 on flexible arms allowing for placement on the superior eyelids. The sides of the eyeglasses frame include arms 558, 560 that press additional electrodes into position generally over the cheekbones. A return electrode can be placed, optionally, as shown at 562, on the neck or upper shoulder of the patient, or elsewhere, if desired.

In some examples, such as that of FIG. 13, a therapy apparatus may also include additional features to make a therapy session more pleasant. For example, the arms 558, 560 may carry speakers or a transducer allowing for sonic bone conduction to offer the patient the ability to listen to music or other entertainment during therapy. In some examples, such an audio functionality may also be used to aid in therapy, such as by having a system deliver instructions related to the therapy by audio. For example, during therapy, to aid in capturing a diagnostic or to establish baseline for a diagnostic, the patient may receive an instruction via the audio subsystem to look in a particular direction, to blink or close the eyes, or to engage in some movement. In other examples, an audio subsystem may be used to deliver placement instruction to the user, by, for example, sensing whether electrode-tissue contact is suboptimal, or whether electrode placement is suboptimal, and providing audio cues to move or enhance placement of one or more electrodes. Such audio subsystems may be provided in any of the other examples shown herein. In some examples, the audio functionality may be included along with video screen functionality described in association with FIG. 10, above.

Figure 14:
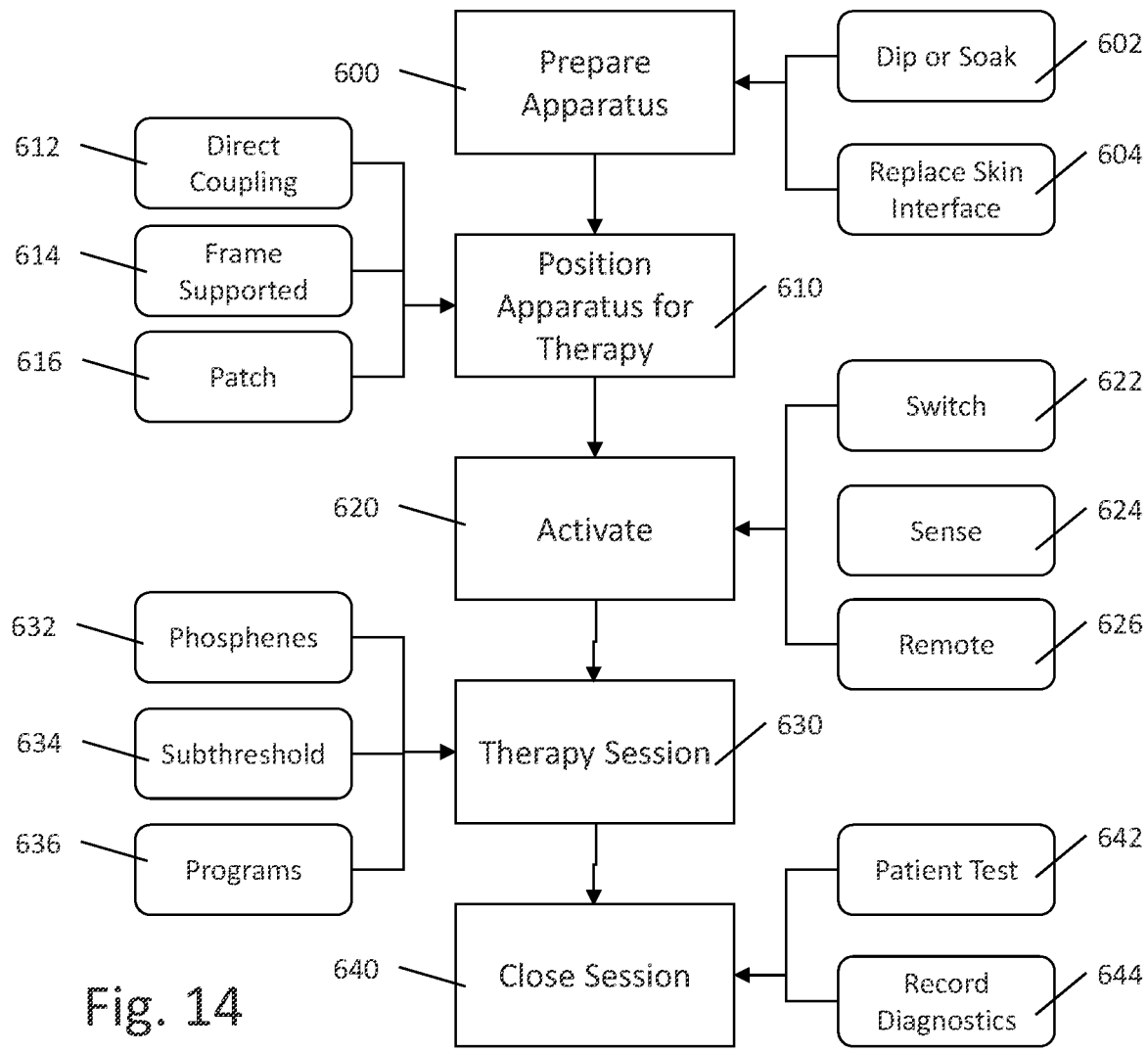
FIG. 14 illustrates, in block form, methods of treatment.

FIG. 14 shows, in block form, a therapy method. The illustrative method comprises preparing a therapy apparatus 600, a step the patient may perform on himself/herself, or which may be performed by another person. In some examples, a skin or tissue contact may be pre-wetted, such as by application of a liquid by spraying, dipping or soaking in a conductive liquid, as indicated at 602. Additionally or alternatively the skin interface, such as a gel or adhesive pad, may be replaced as indicated at 604, whether in the context of single use skin contacts, or reusable skin contacts that are replaced from time to time. In other examples, no electrode preparation is needed.

In some examples, preparing the therapy apparatus comprises only preparing the electrodes, while in other examples a pulse generator is also "prepared". For example, the pulse generator may be turned on or enabled using a physical switch, if desired. Preparation of a pulse generator may include charging to replenish a rechargeable power source (battery or capacitor for example). Preparation may also include pairing the pulse generator with a user remote control such as, for example, if the remote control for the user is provided as an application run on a smartphone or tablet computer, radiofrequency pairing of a pulse generator and the remote control may be performed to prepare for therapy. Once enabled or turned on, the pulse generator may go through diagnostic and/or initialization procedures prior to therapy being available, if desired including, for example, performing an impedance check or an integrity check.

The user then positions the apparatus for therapy delivery, as indicated at 610. Alternatively a caregiver or physician, or other person may perform step 610. This placement may include direct placement as indicated 612, in which the electrical contact itself adheres to tissue to hold a position. Additionally or alternatively, a frame, such as an eyeglasses frame, nosepiece, earpiece, headband, visor, cap or hat, may be used to support the electrode position as indicated at 614. In still other examples, a separate adhesive patch 616 may be provided to augment positioning of the electrical contact. In some examples, the apparatus may be placed on the head, neck or torso, for example. During such placement, the system may measure tissue contact using, for example, measures of impedance or by sensing galvanic skin potential, and may provide feedback to the user or caregiver indicating whether the electrodes are correctly placed.

Next, the system is activated, as indicated at 620. Activation may be performed by the user actuating a switch as indicated at 622, for example, on a frame, patch, or signal generator housing. Additionally or alternatively, the apparatus may be equipped to sense positioning 624, such as to sense temperature at the tissue interface, to sense impedance between electrical contacts, or to sense the galvanic skin potential without injecting a current. Additionally or alternatively, a remote control, such as a user's smartphone, may be used to activate, as indicated at 626. In some examples, both a user input, such as via a switch 622 or remote 626, and device sensing 624 may be used to activate the device.

A therapy session ensues, as indicated at 630. In some examples, a therapy session may be performed to generate phosphenes as a marker of whether therapy is being correctly delivered both in terms of spatial targeting and intensity (which may be defined in terms of one or more of frequency, pulse width and/or amplitude), as indicated at 632. For example, the patient may be provided with a remote control or other feedback device to allow the patient to report observation, or lack of, phosphenes. In another example, electrical signals in and around the eye may be monitored to determine whether phosphenes or other biological activation is occurring as part of block 632. For example, a system may sense, capture, or obtain a pre-therapy set of signal characteristics and compare to a similarly sensed, captured, or obtained signal during, intermittent with, or after therapy.

In some examples, a therapy pattern may be devised with the aim of ensuring effective therapy across a broad volume by modifying the current and voltage loads across several different electrodes to sweep the tissue volume. For example, a system having electrodes at midline (such as on the forehead) and on the right and left eye (such as on the inferior or superior eyelid or lateral canthus). During therapy delivery, a therapy pattern may comprise initially routing 80% of current through the leftmost electrode, then transferring current in subsequent cycles, over a matter of seconds or minutes, to the medial electrode and then to the right-most electrode, such as using a pattern, which may have more or fewer steps, as desired, as follows:

| Left | Midline | Right | Return |
|------|---------|-------|--------|
| +80% | +15% | +5% | −100% |
| +50% | +45% | +5% | −100% |
| +20% | +75% | +5% | −100% |
| +10% | +80% | +10% | −100% |
| +5% | +75% | +20% | −100% |
| +5% | +45% | +50% | −100% |
| +5% | +15% | +80% | −100% |

As the output currents are redistributed among the facial electrodes, the therapy locus is moved across the head. Rather than sweeping across the face from right to left sides, other examples may sweep from lateral to medial positions relative to one eye or the other. Other spatial manipulations may be used. For example, a patient may be queried as to where the patient is observing phosphenes, whether up, down, middle, left or right, with either eye, and current or voltage outputs may be manipulated to ensure that the patient observes phosphenes in multiple spatial locations, to ensure that neural activation takes place in a spatially diverse manner Such field modifications may be used as well with instruction to the user to move his or her eyes to direct vision in a selected direction.

Similar and other spatially varying patterns may be used in a system having three or more electrodes, for example, using four electrodes, with one on each eye and one behind each ear, and varying current load using each of the four electrodes, as by:

| Right Eye | Left Eye | Right Ear | Left Ear | Intensity |
|-----------|----------|-----------|----------|-----------|
| +90% | +10% | −90% | −10% | I(1) |
| +50% | +50% | −90% | −10% | I(2) |
| +50% | +50% | −50% | −50% | I(3) |
| +10% | +90% | −50% | −50% | I(4) |
| +10% | +90% | −10% | −90% | I(5) |

Additional steps may be used, as desired. Right eye and left eye, in this example, may include any of upper or lower eyelid, canthus, palpebral electrode, for example, as well as forehead electrodes placed superior to each eye position. Other sets of unilateral or bilateral positioned electrodes can be used without limitation for like spatial patterns. A pattern may be broadly cyclic to use a sequence as shown with one iteration at each output combination shown, or may, instead, perform a series of output pulses using one configuration before moving to a next configuration, as desired. Within such patterns, variations in intensity (shown above as I(n) in the chart) and/or amplitude can be made to account for the patient's phosphene thresholds for each given electrode selection/position.

Therapy patterns may be manipulated in a large number of ways. In some examples, therapy may take the form of a modulated high frequency output, such as a 1 kHz to 100 kHz (or higher or lower frequency) square wave or sine wave which is modulated at a lower frequency such as 1 Hz to 10 kHz. For example, a 10 kHz square wave (monophasic or biphasic, if desired) may be modulated at 100 to 1000 Hz, with the underlying modulation modified over time to select different modulation frequencies of the high frequency square wave. In other examples, the output may be a shape other than square, such as a decaying output, a triangle wave, or a sine wave. Rather than modifying a modulation frequency, the underlying frequency or "carrier" may be manipulated; for example, a 300 Hz modulation may be applied to a varying carrier having frequencies of 3 kHz, 10 kHz, and 40 kHz, with the carrier frequency changed periodically. Other combinations may be used. A burst therapy may be used, if desired, in which closely spaced impulses are generated, separated by a longer quiescent period.

In some examples, a therapy target may be "subthreshold," 634 wherein the subthreshold approach calls for setting intensity below a phosphene-generating intensity by adjusting one or more of frequency, pulse width, and/or amplitude to prevent, eliminate, and/or avoid phosphene generation. There may be several approaches to a subthreshold therapy regimen. In one example, a user undergoes phosphene threshold-setting periodically under clinical supervision, and one or more of amplitude, pulse width or frequency is then modified to stay below a determined threshold. In another example, during a given therapy session 630, the user may undergo a phosphene thresholding exercise in which therapy is turned on and one or more parameters are varied (such as by raising amplitude) until the user observes phosphenes and provides feedback via a remote control, a pulse generator, or by taking an action such as touching a button on a supporting frame. The user may be instructed to blink several times, for example, to provide a feedback that does not require use of the hands during threshold setting.

Next, one or more control parameters are modified to reduce intensity, such as by one or more of using a narrower pulse width or setting a lower amplitude for a therapy output, or by modifying frequency. Threshold setting may be performed separately for each eye, if desired. Threshold setting may be periodically performed during a session, or it may be performed at the start of a session, or even less frequently as in once a day, once a week, etc. For example, once a phosphene threshold is determined, one or more parameters may be adjusted by some percentage (10%, 20%, 30%, 40%, 50%) or fixed amount (increase or decrease pulse width by 1 to 100 microseconds, decrease amplitude by 100 millivolts or 1 milliamp, or a different amount). A phosphene threshold may be determined at more than one frequency to allow a multiple frequency therapy, such as by establishing the phosphene threshold at 500 Hz and again at 5 kHz, to allow a therapy regimen that uses each of 500 Hz and 5 kHz in an alternating manner A software solution may automatically perform each of thresholding and subsequent parameter setting, for example. By using a subthreshold therapy regimen, the user is allowed ordinary vision during therapy, as the phosphenes generated by a supra-threshold therapy may be distracting or may interfere with performing desired activity such as light chores, watching television, reading, etc.

A therapy session 630 may include the provision of one or more programs 636 that combine more than one therapy type in a sequential or interleaved manner. A sequential therapy program may deliver an output at, for example, a first combination of frequency, pulse width, and/or amplitude, followed by second, third or more combinations. For example, therapy may be delivered at several frequencies over time, such as by delivering a first therapy at a first frequency for a first duration, followed by a second therapy at a second frequency for a second duration, etc. In some examples a program may use different electrode combinations to provide a spatially diverse output, such as by using two close-placed electrodes in a bipolar fashion to target structures in the anterior eye (to enhance tear generation or to encourage fluid flow through the trabeculae), and a monopolar approach with one or more electrodes on the conjunctiva of the eye and a remote electrode to target structures deeper in the eye, such as the retina or optic nerve. Such therapy may be interleaved by delivering one or more monopolar pulses between delivery of bipolar pulses.

A therapy session is then closed, as indicated at 640. Session closing may include testing the patient 642 such as by requesting the patient perform a skill test of visual acuity, for example, and requesting the patient answer one or more questions that may be helpful to understanding therapy success or disease progress. Closing a session may comprise recording diagnostic data 644 related to the output therapy provided (frequency, amplitude, pulse width), measurables during such therapy (impedance being one such measurable, as well as measured/observed phosphenes), and any patient test data. In some examples, a system may comprise a motion sensor to detect eye movements during a therapy session, and such motion may be recorded as well. Any such data may further be offloaded as part of a therapy session by sending to a remote site via the internet through wired, WiFi, or cellular connection, or to another device using, for example, WiFi or Bluetooth communication; in an example, a patient data repository may be provided and accessed via the internet, and closing a session may comprise sending device usage, history and/or diagnostic data to the repository. Optionally a physician may be provided access to the patient data repository for purposes of tracking patient compliance, response to therapy, or any other desirable use.

The following table captures a number of pulse generator housing types and locations, and electrode types, each of which may be used in a variety of combinations for therapy or diagnostic purposes relative to a condition of the eye or other anatomy, with an illustrative list of such conditions:

| Pulse Generator | Electrode | Condition |
| --- | --- | --- |
| In headband | Wettable Electrode (Cellulose, silk, wettable polymer, etc.) | Dry or wet macular degeneration |
| In earpiece | Bare metal | Inherited retinal disease |
| In armband | Wet electrode using hydrogel or gel patch | Presbyopia |
| In neckpiece | Dry electrode (multilayer metal and polymer) | Diabetic retinopathy |
| In glasses frame | Expandable (luminal) as in FIG. 8 | Glaucoma |
| Wearable on torso | Any of the above, with hinged or not-hinged coupling to frame | Retinitis pigmentosa |
| In eyepiece | Attachable to eyelashes | Startgardt's |
| On temple (FIG. 11) | | Retinal venous or arterial stenosis or occlusion |

The list is not intended to indicate that a particular pulse generator and electrode is useful for the condition shown on the same row; instead, an entry from each column may be used with any of the entries in any of the other two columns. The conditions listed are typically more prevalent; other conditions are also listed above in addition to those in the table. Some other conditions may include, but are not limited to, CMV-retinitis, Best's disease, macular dystrophy, optic neuritis, ischemic anterior optic neuritis, Usher's syndrome, Leber's congenital amaurosis, cone-rod dystrophy, cone dystrophy, choroideremia and gyrate atrophy, central serous chorioretinopathy, cystoid macular edema, ocular histoplasmosis, ocular toxoplasmosis, retinopathy of prematurity, amblyopia, strabismus, and nystagmus.

Pulse generators may use any suitable power supply configuration, including the use of primary cell batteries (whether replaceable or not), rechargeable batteries, chargeable non-battery storage (such as a capacitor), and externally powered systems that rely on a wireless, magnetic or other power coupling to receive power when therapy is needed, without longer term power storage capability. Some approaches to power supply are shown and described in U.S. patent application Ser. No. 16/844,421, filed on Apr. 9, 2020, titled SYSTEMS AND INTERFACES FOR OCULAR THERAPY, the disclosure of which is incorporated herein by reference, such as at FIGS. 8-10 thereof.

Following are a number of illustrative example methods for bipolar therapy. In addition to this list, each noted position for an electrode may be used in left/right configurations, such as by delivering a therapy or diagnostic signal between an electrode on the right superior eyelid and an electrode on the left superior eyelid, or between an electrode on the right medial canthus and an electrode on the left lateral canthus. Each of these methods may be executed or performed by an apparatus for treating a condition of the eye comprising a pulse generator coupled to a plurality of electrodes, the pulse generator comprising circuitry including a controller configured to perform a method of treating an eye condition by delivery of therapy between at least first and second electrodes. Further each of these methods, when performed by such an apparatus, would be performed using an apparatus having first and second electrodes adapted for the placements recited in the method, where examples of electrodes adapted for each such placement are described in the examples of FIGS. 1-13, and the methods are described (with additional steps that may optionally be added or included) in FIG. 14.

An illustrative, non-limiting example takes the form of a method of treating an eye condition comprising delivering therapy between a first electrode placed on the inferior eyelid and a second electrode placed on the superior eyelid.

An illustrative, non-limiting example takes the form of a method of treating an eye condition comprising delivering therapy between a first electrode placed on the inferior eyelid and a second electrode placed on the conjunctiva.

An illustrative, non-limiting example takes the form of a method of treating an eye condition comprising delivering therapy between a first electrode placed on the inferior eyelid and a second electrode placed on the medial canthus.

An illustrative, non-limiting example takes the form of a method of treating an eye condition comprising delivering therapy between a first electrode placed on the inferior eyelid and a second electrode placed on the lateral canthus.

An illustrative, non-limiting example takes the form of a method of treating an eye condition comprising delivering therapy between a first electrode placed on the inferior eyelid and a second electrode placed on the forehead.

An illustrative, non-limiting example takes the form of a method of treating an eye condition comprising delivering therapy between a first electrode placed on the inferior eyelid and a second electrode placed medial of the medial canthus.

An illustrative, non-limiting example takes the form of a method of treating an eye condition comprising delivering therapy between a first electrode placed on the inferior eyelid and a second electrode placed on the side of the bridge of the nose.

An illustrative, non-limiting example takes the form of a method of treating an eye condition comprising delivering therapy between a first electrode placed on the inferior eyelid and a second electrode placed on the temple.

An illustrative, non-limiting example takes the form of a method of treating an eye condition comprising delivering therapy between a first electrode placed on the inferior eyelid and a second electrode placed lateral to the lateral canthus.

An illustrative, non-limiting example takes the form of a method of treating an eye condition comprising delivering therapy between a first electrode placed on the inferior eyelid and a second electrode placed on the skin over the mandible.

An illustrative, non-limiting example takes the form of a method of treating an eye condition comprising delivering therapy between a first electrode placed on the inferior eyelid and a second electrode placed in the lacrimal puncta.

An illustrative, non-limiting example takes the form of a method of treating an eye condition comprising delivering therapy between a first electrode placed on the inferior eyelid and a second electrode placed on the eye itself.

An illustrative, non-limiting example takes the form of a method of treating an eye condition comprising delivering therapy between a first electrode placed on the inferior eyelid and a second electrode placed in the nasal cavity.

An illustrative, non-limiting example takes the form of a method of treating an eye condition comprising delivering therapy between a first electrode placed on the inferior eyelid and a second electrode placed in the nasolacrimal duct.

An illustrative, non-limiting example takes the form of a method of treating an eye condition comprising delivering therapy between a first electrode placed on the superior eyelid and a second electrode placed on the conjunctiva.

An illustrative, non-limiting example takes the form of a method of treating an eye condition comprising delivering therapy between a first electrode placed on the superior eyelid and a second electrode placed on the medial canthus.

An illustrative, non-limiting example takes the form of a method of treating an eye condition comprising delivering therapy between a first electrode placed on the superior eyelid and a second electrode placed on the lateral canthus.

An illustrative, non-limiting example takes the form of a method of treating an eye condition comprising delivering therapy between a first electrode placed on the superior eyelid and a second electrode placed on the forehead.

An illustrative, non-limiting example takes the form of a method of treating an eye condition comprising delivering therapy between a first electrode placed on the superior eyelid and a second electrode placed medial of the medial canthus.

An illustrative, non-limiting example takes the form of a method of treating an eye condition comprising delivering therapy between a first electrode placed on the superior eyelid and a second electrode placed on the side of the bridge of the nose.

An illustrative, non-limiting example takes the form of a method of treating an eye condition comprising delivering therapy between a first electrode placed on the superior eyelid and a second electrode placed on the temple.

An illustrative, non-limiting example takes the form of a method of treating an eye condition comprising delivering therapy between a first electrode placed on the superior eyelid and a second electrode placed lateral to the lateral canthus.

An illustrative, non-limiting example takes the form of a method of treating an eye condition comprising delivering therapy between a first electrode placed on the superior eyelid and a second electrode placed on the skin over the mandible.

An illustrative, non-limiting example takes the form of a method of treating an eye condition comprising delivering therapy between a first electrode placed on the superior eyelid and a second electrode placed in the lacrimal puncta.

An illustrative, non-limiting example takes the form of a method of treating an eye condition comprising delivering therapy between a first electrode placed on the superior eyelid and a second electrode placed on the eye itself.

An illustrative, non-limiting example takes the form of a method of treating an eye condition comprising delivering therapy between a first electrode placed on the superior eyelid and a second electrode placed in the nasal cavity.

An illustrative, non-limiting example takes the form of a method of treating an eye condition comprising delivering therapy between a first electrode placed on the superior eyelid and a second electrode placed in the nasolacrimal duct.

An illustrative, non-limiting example takes the form of a method of treating an eye condition comprising delivering therapy between a first electrode placed on the conjunctiva and a second electrode placed on the medial canthus.

An illustrative, non-limiting example takes the form of a method of treating an eye condition comprising delivering therapy between a first electrode placed on the conjunctiva and a second electrode placed on the lateral canthus.

An illustrative, non-limiting example takes the form of a method of treating an eye condition comprising delivering therapy between a first electrode placed on the conjunctiva and a second electrode placed on the forehead.

An illustrative, non-limiting example takes the form of a method of treating an eye condition comprising delivering therapy between a first electrode placed on the conjunctiva and a second electrode placed medial of the medial canthus.

An illustrative, non-limiting example takes the form of a method of treating an eye condition comprising delivering therapy between a first electrode placed on the conjunctiva and a second electrode placed on the side of the bridge of the nose.

An illustrative, non-limiting example takes the form of a method of treating an eye condition comprising delivering therapy between a first electrode placed on the conjunctiva and a second electrode placed on the temple.

An illustrative, non-limiting example takes the form of a method of treating an eye condition comprising delivering therapy between a first electrode placed on the conjunctiva and a second electrode placed lateral to the lateral canthus.

An illustrative, non-limiting example takes the form of a method of treating an eye condition comprising delivering therapy between a first electrode placed on the conjunctiva and a second electrode placed on the skin over the mandible.

An illustrative, non-limiting example takes the form of a method of treating an eye condition comprising delivering therapy between a first electrode placed on the conjunctiva and a second electrode placed in the lacrimal puncta.

An illustrative, non-limiting example takes the form of a method of treating an eye condition comprising delivering therapy between a first electrode placed on the conjunctiva and a second electrode placed on the eye itself.

An illustrative, non-limiting example takes the form of a method of treating an eye condition comprising delivering therapy between a first electrode placed on the conjunctiva and a second electrode placed in the nasal cavity.

An illustrative, non-limiting example takes the form of a method of treating an eye condition comprising delivering therapy between a first electrode placed on the conjunctiva and a second electrode placed in the nasolacrimal duct.

An illustrative, non-limiting example takes the form of a method of treating an eye condition comprising delivering therapy between a first electrode placed on the medial canthus and a second electrode placed on the lateral canthus.

An illustrative, non-limiting example takes the form of a method of treating an eye condition comprising delivering therapy between a first electrode placed on the medial canthus and a second electrode placed on the forehead.

An illustrative, non-limiting example takes the form of a method of treating an eye condition comprising delivering therapy between a first electrode placed on the medial canthus and a second electrode placed medial of the medial canthus.

An illustrative, non-limiting example takes the form of a method of treating an eye condition comprising delivering therapy between a first electrode placed on the medial canthus and a second electrode placed on the side of the bridge of the nose.

An illustrative, non-limiting example takes the form of a method of treating an eye condition comprising delivering therapy between a first electrode placed on the medial canthus and a second electrode placed on the temple.

An illustrative, non-limiting example takes the form of a method of treating an eye condition comprising delivering therapy between a first electrode placed on the medial canthus and a second electrode placed lateral to the lateral canthus.

An illustrative, non-limiting example takes the form of a method of treating an eye condition comprising delivering therapy between a first electrode placed on the medial canthus and a second electrode placed on the skin over the mandible.

An illustrative, non-limiting example takes the form of a method of treating an eye condition comprising delivering therapy between a first electrode placed on the medial canthus and a second electrode placed in the lacrimal puncta.

An illustrative, non-limiting example takes the form of a method of treating an eye condition comprising delivering therapy between a first electrode placed on the medial canthus and a second electrode placed on the eye itself.

An illustrative, non-limiting example takes the form of a method of treating an eye condition comprising delivering therapy between a first electrode placed on the medial canthus and a second electrode placed in the nasal cavity.

An illustrative, non-limiting example takes the form of a method of treating an eye condition comprising delivering therapy between a first electrode placed on the medial canthus and a second electrode placed in the nasolacrimal duct.

An illustrative, non-limiting example takes the form of a method of treating an eye condition comprising delivering therapy between a first electrode placed on the lateral canthus and a second electrode placed on the forehead.

An illustrative, non-limiting example takes the form of a method of treating an eye condition comprising delivering therapy between a first electrode placed on the lateral canthus and a second electrode placed medial of the medial canthus.

An illustrative, non-limiting example takes the form of a method of treating an eye condition comprising delivering therapy between a first electrode placed on the lateral canthus and a second electrode placed on the side of the bridge of the nose.

An illustrative, non-limiting example takes the form of a method of treating an eye condition comprising delivering therapy between a first electrode placed on the lateral canthus and a second electrode placed on the temple.

An illustrative, non-limiting example takes the form of a method of treating an eye condition comprising delivering therapy between a first electrode placed on the lateral canthus and a second electrode placed lateral to the lateral canthus.

An illustrative, non-limiting example takes the form of a method of treating an eye condition comprising delivering therapy between a first electrode placed on the lateral canthus and a second electrode placed on the skin over the mandible.

An illustrative, non-limiting example takes the form of a method of treating an eye condition comprising delivering therapy between a first electrode placed on the lateral canthus and a second electrode placed in the lacrimal puncta.

An illustrative, non-limiting example takes the form of a method of treating an eye condition comprising delivering therapy between a first electrode placed on the lateral canthus and a second electrode placed on the eye itself.

An illustrative, non-limiting example takes the form of a method of treating an eye condition comprising delivering therapy between a first electrode placed on the lateral canthus and a second electrode placed in the nasal cavity.

An illustrative, non-limiting example takes the form of a method of treating an eye condition comprising delivering therapy between a first electrode placed on the lateral canthus and a second electrode placed in the nasolacrimal duct.

An illustrative, non-limiting example takes the form of a method of treating an eye condition comprising delivering therapy between a first electrode placed on the forehead and a second electrode placed medial of the medial canthus.

An illustrative, non-limiting example takes the form of a method of treating an eye condition comprising delivering therapy between a first electrode placed on the forehead and a second electrode placed on the side of the bridge of the nose.

An illustrative, non-limiting example takes the form of a method of treating an eye condition comprising delivering therapy between a first electrode placed on the forehead and a second electrode placed on the temple.

An illustrative, non-limiting example takes the form of a method of treating an eye condition comprising delivering therapy between a first electrode placed on the forehead and a second electrode placed lateral to the lateral canthus.

An illustrative, non-limiting example takes the form of a method of treating an eye condition comprising delivering therapy between a first electrode placed on the forehead and a second electrode placed on the skin over the mandible.

An illustrative, non-limiting example takes the form of a method of treating an eye condition comprising delivering therapy between a first electrode placed on the forehead and a second electrode placed in the lacrimal puncta.

An illustrative, non-limiting example takes the form of a method of treating an eye condition comprising delivering therapy between a first electrode placed on the forehead and a second electrode placed on the eye itself.

An illustrative, non-limiting example takes the form of a method of treating an eye condition comprising delivering therapy between a first electrode placed on the forehead and a second electrode placed in the nasal cavity.

An illustrative, non-limiting example takes the form of a method of treating an eye condition comprising delivering therapy between a first electrode placed on the forehead and a second electrode placed in the nasolacrimal duct.

An illustrative, non-limiting example takes the form of a method of treating an eye condition comprising delivering therapy between a first electrode placed medial of the medial canthus and a second electrode placed on the side of the bridge of the nose.

An illustrative, non-limiting example takes the form of a method of treating an eye condition comprising delivering therapy between a first electrode placed medial of the medial canthus and a second electrode placed on the temple.

An illustrative, non-limiting example takes the form of a method of treating an eye condition comprising delivering therapy between a first electrode placed medial of the medial canthus and a second electrode placed lateral to the lateral canthus.

An illustrative, non-limiting example takes the form of a method of treating an eye condition comprising delivering therapy between a first electrode placed medial of the medial canthus and a second electrode placed on the skin over the mandible.

An illustrative, non-limiting example takes the form of a method of treating an eye condition comprising delivering therapy between a first electrode placed medial of the medial canthus and a second electrode placed in the lacrimal puncta.

An illustrative, non-limiting example takes the form of a method of treating an eye condition comprising delivering therapy between a first electrode placed medial of the medial canthus and a second electrode placed on the eye itself.

An illustrative, non-limiting example takes the form of a method of treating an eye condition comprising delivering therapy between a first electrode placed medial of the medial canthus and a second electrode placed in the nasal cavity.

An illustrative, non-limiting example takes the form of a method of treating an eye condition comprising delivering therapy between a first electrode placed medial of the medial canthus and a second electrode placed in the nasolacrimal duct.

An illustrative, non-limiting example takes the form of a method of treating an eye condition comprising delivering therapy between a first electrode placed on the side of the bridge of the nose and a second electrode placed on the temple.

An illustrative, non-limiting example takes the form of a method of treating an eye condition comprising delivering therapy between a first electrode placed on the side of the bridge of the nose and a second electrode placed lateral to the lateral canthus.

An illustrative, non-limiting example takes the form of a method of treating an eye condition comprising delivering therapy between a first electrode placed on the side of the bridge of the nose and a second electrode placed on the skin over the mandible.

An illustrative, non-limiting example takes the form of a method of treating an eye condition comprising delivering therapy between a first electrode placed on the side of the bridge of the nose and a second electrode placed in the lacrimal puncta.

An illustrative, non-limiting example takes the form of a method of treating an eye condition comprising delivering therapy between a first electrode placed on the side of the bridge of the nose and a second electrode placed on the eye itself.

An illustrative, non-limiting example takes the form of a method of treating an eye condition comprising delivering therapy between a first electrode placed on the side of the bridge of the nose and a second electrode placed in the nasal cavity.

An illustrative, non-limiting example takes the form of a method of treating an eye condition comprising delivering therapy between a first electrode placed on the side of the bridge of the nose and a second electrode placed in the nasolacrimal duct.

An illustrative, non-limiting example takes the form of a method of treating an eye condition comprising delivering therapy between a first electrode placed on the temple and a second electrode placed lateral to the lateral canthus.

An illustrative, non-limiting example takes the form of a method of treating an eye condition comprising delivering therapy between a first electrode placed on the temple and a second electrode placed on the skin over the mandible.

An illustrative, non-limiting example takes the form of a method of treating an eye condition comprising delivering therapy between a first electrode placed on the temple and a second electrode placed in the lacrimal puncta.

An illustrative, non-limiting example takes the form of a method of treating an eye condition comprising delivering therapy between a first electrode placed on the temple and a second electrode placed on the eye itself.

An illustrative, non-limiting example takes the form of a method of treating an eye condition comprising delivering therapy between a first electrode placed on the temple and a second electrode placed in the nasal cavity.

An illustrative, non-limiting example takes the form of a method of treating an eye condition comprising delivering therapy between a first electrode placed on the temple and a second electrode placed in the nasolacrimal duct.

An illustrative, non-limiting example takes the form of a method of treating an eye condition comprising delivering therapy between a first electrode placed lateral to the lateral canthus and a second electrode placed on the skin over the mandible.

An illustrative, non-limiting example takes the form of a method of treating an eye condition comprising delivering therapy between a first electrode placed lateral to the lateral canthus and a second electrode placed in the lacrimal puncta.

An illustrative, non-limiting example takes the form of a method of treating an eye condition comprising delivering therapy between a first electrode placed lateral to the lateral canthus and a second electrode placed on the eye itself.

An illustrative, non-limiting example takes the form of a method of treating an eye condition comprising delivering therapy between a first electrode placed lateral to the lateral canthus and a second electrode placed in the nasal cavity.

An illustrative, non-limiting example takes the form of a method of treating an eye condition comprising delivering therapy between a first electrode placed lateral to the lateral canthus and a second electrode placed in the nasolacrimal duct.

An illustrative, non-limiting example takes the form of a method of treating an eye condition comprising delivering therapy between a first electrode placed on the skin over the mandible and a second electrode placed in the lacrimal puncta.

An illustrative, non-limiting example takes the form of a method of treating an eye condition comprising delivering therapy between a first electrode placed on the skin over the mandible and a second electrode placed on the eye itself.

An illustrative, non-limiting example takes the form of a method of treating an eye condition comprising delivering therapy between a first electrode placed on the skin over the mandible and a second electrode placed in the nasal cavity.

An illustrative, non-limiting example takes the form of a method of treating an eye condition comprising delivering therapy between a first electrode placed on the skin over the mandible and a second electrode placed in the nasolacrimal duct.

An illustrative, non-limiting example takes the form of a method of treating an eye condition comprising delivering therapy between a first electrode placed in the lacrimal puncta and a second electrode placed on the eye itself.

An illustrative, non-limiting example takes the form of a method of treating an eye condition comprising delivering therapy between a first electrode placed in the lacrimal puncta and a second electrode placed in the nasal cavity.

An illustrative, non-limiting example takes the form of a method of treating an eye condition comprising delivering therapy between a first electrode placed in the lacrimal puncta and a second electrode placed in the nasolacrimal duct.

An illustrative, non-limiting example takes the form of a method of treating an eye condition comprising delivering therapy between a first electrode placed on the eye itself and a second electrode placed in the nasal cavity.

An illustrative, non-limiting example takes the form of a method of treating an eye condition comprising delivering therapy between a first electrode placed on the eye itself and a second electrode placed in the nasolacrimal duct.

An illustrative, non-limiting example takes the form of a method of treating an eye condition comprising delivering therapy between a first electrode placed in the nasal cavity and a second electrode placed in the nasolacrimal duct.

Following are a list of monopolar method examples. Within this list, each noted position for an electrode may be used on either right or left side of the patient, and further some monopolar configurations may deliver therapy to both the left and right side at once, for example, by having left and right eyelid electrodes delivering the same output (or even as a common pole) relative to a distant electrode placed for example on the torso.

An illustrative, non-limiting example takes the form of a method of treating an eye condition comprising delivering therapy between a first electrode placed on the inferior eyelid and a second electrode placed behind the ear.

An illustrative, non-limiting example takes the form of a method of treating an eye condition comprising delivering therapy between a first electrode placed on the inferior eyelid and a second electrode placed on the ear.

An illustrative, non-limiting example takes the form of a method of treating an eye condition comprising delivering therapy between a first electrode placed on the inferior eyelid and a second electrode placed on the neck.

An illustrative, non-limiting example takes the form of a method of treating an eye condition comprising delivering therapy between a first electrode placed on the inferior eyelid and a second electrode placed on the back of the head.

An illustrative, non-limiting example takes the form of a method of treating an eye condition comprising delivering therapy between a first electrode placed on the inferior eyelid and a second electrode placed on the chest, shoulder or back.

An illustrative, non-limiting example takes the form of a method of treating an eye condition comprising delivering therapy between a first electrode placed on the inferior eyelid and a second electrode placed on the torso.

An illustrative, non-limiting example takes the form of a method of treating an eye condition comprising delivering therapy between a first electrode placed on the inferior eyelid and a second electrode placed on a limb.

An illustrative, non-limiting example takes the form of a method of treating an eye condition comprising delivering therapy between a first electrode placed on the inferior eyelid and a second electrode placed on an extremity.

An illustrative, non-limiting example takes the form of a method of treating an eye condition comprising delivering therapy between a first electrode placed on the superior eyelid and a second electrode placed behind the ear.

An illustrative, non-limiting example takes the form of a method of treating an eye condition comprising delivering therapy between a first electrode placed on the superior eyelid and a second electrode placed on the ear.

An illustrative, non-limiting example takes the form of a method of treating an eye condition comprising delivering therapy between a first electrode placed on the superior eyelid and a second electrode placed on the neck.

An illustrative, non-limiting example takes the form of a method of treating an eye condition comprising delivering therapy between a first electrode placed on the superior eyelid and a second electrode placed on the back of the head.

An illustrative, non-limiting example takes the form of a method of treating an eye condition comprising delivering therapy between a first electrode placed on the superior eyelid and a second electrode placed on the chest, shoulder or back.

An illustrative, non-limiting example takes the form of a method of treating an eye condition comprising delivering therapy between a first electrode placed on the superior eyelid and a second electrode placed on the torso.

An illustrative, non-limiting example takes the form of a method of treating an eye condition comprising delivering therapy between a first electrode placed on the superior eyelid and a second electrode placed on a limb.

An illustrative, non-limiting example takes the form of a method of treating an eye condition comprising delivering therapy between a first electrode placed on the superior eyelid and a second electrode placed on an extremity.

An illustrative, non-limiting example takes the form of a method of treating an eye condition comprising delivering therapy between a first electrode placed on the conjunctiva and a second electrode placed behind the ear.

An illustrative, non-limiting example takes the form of a method of treating an eye condition comprising delivering therapy between a first electrode placed on the conjunctiva and a second electrode placed on the ear.

An illustrative, non-limiting example takes the form of a method of treating an eye condition comprising delivering therapy between a first electrode placed on the conjunctiva and a second electrode placed on the neck.

An illustrative, non-limiting example takes the form of a method of treating an eye condition comprising delivering therapy between a first electrode placed on the conjunctiva and a second electrode placed on the back of the head.

An illustrative, non-limiting example takes the form of a method of treating an eye condition comprising delivering therapy between a first electrode placed on the conjunctiva and a second electrode placed on the chest, shoulder or back.

An illustrative, non-limiting example takes the form of a method of treating an eye condition comprising delivering therapy between a first electrode placed on the conjunctiva and a second electrode placed on the torso.

An illustrative, non-limiting example takes the form of a method of treating an eye condition comprising delivering therapy between a first electrode placed on the conjunctiva and a second electrode placed on a limb.

An illustrative, non-limiting example takes the form of a method of treating an eye condition comprising delivering therapy between a first electrode placed on the conjunctiva and a second electrode placed on an extremity.

An illustrative, non-limiting example takes the form of a method of treating an eye condition comprising delivering therapy between a first electrode placed on the medial canthus and a second electrode placed behind the ear.

An illustrative, non-limiting example takes the form of a method of treating an eye condition comprising delivering therapy between a first electrode placed on the medial canthus and a second electrode placed on the ear.

An illustrative, non-limiting example takes the form of a method of treating an eye condition comprising delivering therapy between a first electrode placed on the medial canthus and a second electrode placed on the neck.

An illustrative, non-limiting example takes the form of a method of treating an eye condition comprising delivering therapy between a first electrode placed on the medial canthus and a second electrode placed on the back of the head.

An illustrative, non-limiting example takes the form of a method of treating an eye condition comprising delivering therapy between a first electrode placed on the medial canthus and a second electrode placed on the chest, shoulder or back.

An illustrative, non-limiting example takes the form of a method of treating an eye condition comprising delivering therapy between a first electrode placed on the medial canthus and a second electrode placed on the torso.

An illustrative, non-limiting example takes the form of a method of treating an eye condition comprising delivering therapy between a first electrode placed on the medial canthus and a second electrode placed on a limb.

An illustrative, non-limiting example takes the form of a method of treating an eye condition comprising delivering therapy between a first electrode placed on the medial canthus and a second electrode placed on an extremity.

An illustrative, non-limiting example takes the form of a method of treating an eye condition comprising delivering therapy between a first electrode placed on the lateral canthus and a second electrode placed behind the ear.

An illustrative, non-limiting example takes the form of a method of treating an eye condition comprising delivering therapy between a first electrode placed on the lateral canthus and a second electrode placed on the ear.

An illustrative, non-limiting example takes the form of a method of treating an eye condition comprising delivering therapy between a first electrode placed on the lateral canthus and a second electrode placed on the neck.

An illustrative, non-limiting example takes the form of a method of treating an eye condition comprising delivering therapy between a first electrode placed on the lateral canthus and a second electrode placed on the back of the head.

An illustrative, non-limiting example takes the form of a method of treating an eye condition comprising delivering therapy between a first electrode placed on the lateral canthus and a second electrode placed on the chest, shoulder or back.

An illustrative, non-limiting example takes the form of a method of treating an eye condition comprising delivering therapy between a first electrode placed on the lateral canthus and a second electrode placed on the torso.

An illustrative, non-limiting example takes the form of a method of treating an eye condition comprising delivering therapy between a first electrode placed on the lateral canthus and a second electrode placed on a limb.

An illustrative, non-limiting example takes the form of a method of treating an eye condition comprising delivering therapy between a first electrode placed on the lateral canthus and a second electrode placed on an extremity.

An illustrative, non-limiting example takes the form of a method of treating an eye condition comprising delivering therapy between a first electrode placed on the forehead and a second electrode placed behind the ear.

An illustrative, non-limiting example takes the form of a method of treating an eye condition comprising delivering therapy between a first electrode placed on the forehead and a second electrode placed on the ear.

An illustrative, non-limiting example takes the form of a method of treating an eye condition comprising delivering therapy between a first electrode placed on the forehead and a second electrode placed on the neck.

An illustrative, non-limiting example takes the form of a method of treating an eye condition comprising delivering therapy between a first electrode placed on the forehead and a second electrode placed on the back of the head.

An illustrative, non-limiting example takes the form of a method of treating an eye condition comprising delivering therapy between a first electrode placed on the forehead and a second electrode placed on the chest, shoulder or back.

An illustrative, non-limiting example takes the form of a method of treating an eye condition comprising delivering therapy between a first electrode placed on the forehead and a second electrode placed on the torso.

An illustrative, non-limiting example takes the form of a method of treating an eye condition comprising delivering therapy between a first electrode placed on the forehead and a second electrode placed on a limb.

An illustrative, non-limiting example takes the form of a method of treating an eye condition comprising delivering therapy between a first electrode placed on the forehead and a second electrode placed on an extremity.

An illustrative, non-limiting example takes the form of a method of treating an eye condition comprising delivering therapy between a first electrode placed medial of the medial canthus and a second electrode placed behind the ear.

An illustrative, non-limiting example takes the form of a method of treating an eye condition comprising delivering therapy between a first electrode placed medial of the medial canthus and a second electrode placed on the ear.

An illustrative, non-limiting example takes the form of a method of treating an eye condition comprising delivering therapy between a first electrode placed medial of the medial canthus and a second electrode placed on the neck.

An illustrative, non-limiting example takes the form of a method of treating an eye condition comprising delivering therapy between a first electrode placed medial of the medial canthus and a second electrode placed on the back of the head.

An illustrative, non-limiting example takes the form of a method of treating an eye condition comprising delivering therapy between a first electrode placed medial of the medial canthus and a second electrode placed on the chest, shoulder or back.

An illustrative, non-limiting example takes the form of a method of treating an eye condition comprising delivering therapy between a first electrode placed medial of the medial canthus and a second electrode placed on the torso.

An illustrative, non-limiting example takes the form of a method of treating an eye condition comprising delivering therapy between a first electrode placed medial of the medial canthus and a second electrode placed on a limb.

An illustrative, non-limiting example takes the form of a method of treating an eye condition comprising delivering therapy between a first electrode placed medial of the medial canthus and a second electrode placed on an extremity.

An illustrative, non-limiting example takes the form of a method of treating an eye condition comprising delivering therapy between a first electrode placed on the side of the bridge of the nose and a second electrode placed behind the ear.

An illustrative, non-limiting example takes the form of a method of treating an eye condition comprising delivering therapy between a first electrode placed on the side of the bridge of the nose and a second electrode placed on the ear.

An illustrative, non-limiting example takes the form of a method of treating an eye condition comprising delivering therapy between a first electrode placed on the side of the bridge of the nose and a second electrode placed on the neck.

An illustrative, non-limiting example takes the form of a method of treating an eye condition comprising delivering therapy between a first electrode placed on the side of the bridge of the nose and a second electrode placed on the back of the head.

An illustrative, non-limiting example takes the form of a method of treating an eye condition comprising delivering therapy between a first electrode placed on the side of the bridge of the nose and a second electrode placed on the chest, shoulder or back.

An illustrative, non-limiting example takes the form of a method of treating an eye condition comprising delivering therapy between a first electrode placed on the side of the bridge of the nose and a second electrode placed on the torso.

An illustrative, non-limiting example takes the form of a method of treating an eye condition comprising delivering therapy between a first electrode placed on the side of the bridge of the nose and a second electrode placed on a limb.

An illustrative, non-limiting example takes the form of a method of treating an eye condition comprising delivering therapy between a first electrode placed on the side of the bridge of the nose and a second electrode placed on an extremity.

An illustrative, non-limiting example takes the form of a method of treating an eye condition comprising delivering therapy between a first electrode placed on the temple and a second electrode placed behind the ear.

An illustrative, non-limiting example takes the form of a method of treating an eye condition comprising delivering therapy between a first electrode placed on the temple and a second electrode placed on the ear.

An illustrative, non-limiting example takes the form of a method of treating an eye condition comprising delivering therapy between a first electrode placed on the temple and a second electrode placed on the neck.

An illustrative, non-limiting example takes the form of a method of treating an eye condition comprising delivering therapy between a first electrode placed on the temple and a second electrode placed on the back of the head.

An illustrative, non-limiting example takes the form of a method of treating an eye condition comprising delivering therapy between a first electrode placed on the temple and a second electrode placed on the chest, shoulder or back.

An illustrative, non-limiting example takes the form of a method of treating an eye condition comprising delivering therapy between a first electrode placed on the temple and a second electrode placed on the torso.

An illustrative, non-limiting example takes the form of a method of treating an eye condition comprising delivering therapy between a first electrode placed on the temple and a second electrode placed on a limb.

An illustrative, non-limiting example takes the form of a method of treating an eye condition comprising delivering therapy between a first electrode placed on the temple and a second electrode placed on an extremity.

An illustrative, non-limiting example takes the form of a method of treating an eye condition comprising delivering therapy between a first electrode placed lateral to the lateral canthus and a second electrode placed behind the ear.

An illustrative, non-limiting example takes the form of a method of treating an eye condition comprising delivering therapy between a first electrode placed lateral to the lateral canthus and a second electrode placed on the ear.

An illustrative, non-limiting example takes the form of a method of treating an eye condition comprising delivering therapy between a first electrode placed lateral to the lateral canthus and a second electrode placed on the neck.

An illustrative, non-limiting example takes the form of a method of treating an eye condition comprising delivering therapy between a first electrode placed lateral to the lateral canthus and a second electrode placed on the back of the head.

An illustrative, non-limiting example takes the form of a method of treating an eye condition comprising delivering therapy between a first electrode placed lateral to the lateral canthus and a second electrode placed on the chest, shoulder or back.

An illustrative, non-limiting example takes the form of a method of treating an eye condition comprising delivering therapy between a first electrode placed lateral to the lateral canthus and a second electrode placed on the torso.

An illustrative, non-limiting example takes the form of a method of treating an eye condition comprising delivering therapy between a first electrode placed lateral to the lateral canthus and a second electrode placed on a limb.

An illustrative, non-limiting example takes the form of a method of treating an eye condition comprising delivering therapy between a first electrode placed lateral to the lateral canthus and a second electrode placed on an extremity.

An illustrative, non-limiting example takes the form of a method of treating an eye condition comprising delivering therapy between a first electrode placed on the skin over the mandible and a second electrode placed behind the ear.

An illustrative, non-limiting example takes the form of a method of treating an eye condition comprising delivering therapy between a first electrode placed on the skin over the mandible and a second electrode placed on the ear.

An illustrative, non-limiting example takes the form of a method of treating an eye condition comprising delivering therapy between a first electrode placed on the skin over the mandible and a second electrode placed on the neck.

An illustrative, non-limiting example takes the form of a method of treating an eye condition comprising delivering therapy between a first electrode placed on the skin over the mandible and a second electrode placed on the back of the head.

An illustrative, non-limiting example takes the form of a method of treating an eye condition comprising delivering therapy between a first electrode placed on the skin over the mandible and a second electrode placed on the chest, shoulder or back.

An illustrative, non-limiting example takes the form of a method of treating an eye condition comprising delivering therapy between a first electrode placed on the skin over the mandible and a second electrode placed on the torso.

An illustrative, non-limiting example takes the form of a method of treating an eye condition comprising delivering therapy between a first electrode placed on the skin over the mandible and a second electrode placed on a limb.

An illustrative, non-limiting example takes the form of a method of treating an eye condition comprising delivering therapy between a first electrode placed on the skin over the mandible and a second electrode placed on an extremity.

An illustrative, non-limiting example takes the form of a method of treating an eye condition comprising delivering therapy between a first electrode placed in the lacrimal puncta and a second electrode placed behind the ear.

An illustrative, non-limiting example takes the form of a method of treating an eye condition comprising delivering therapy between a first electrode placed in the lacrimal puncta and a second electrode placed on the ear.

An illustrative, non-limiting example takes the form of a method of treating an eye condition comprising delivering therapy between a first electrode placed in the lacrimal puncta and a second electrode placed on the neck.

An illustrative, non-limiting example takes the form of a method of treating an eye condition comprising delivering therapy between a first electrode placed in the lacrimal puncta and a second electrode placed on the back of the head.

An illustrative, non-limiting example takes the form of a method of treating an eye condition comprising delivering therapy between a first electrode placed in the lacrimal puncta and a second electrode placed on the chest, shoulder or back.

An illustrative, non-limiting example takes the form of a method of treating an eye condition comprising delivering therapy between a first electrode placed in the lacrimal puncta and a second electrode placed on the torso.

An illustrative, non-limiting example takes the form of a method of treating an eye condition comprising delivering therapy between a first electrode placed in the lacrimal puncta and a second electrode placed on a limb.

An illustrative, non-limiting example takes the form of a method of treating an eye condition comprising delivering therapy between a first electrode placed in the lacrimal puncta and a second electrode placed on an extremity.

An illustrative, non-limiting example takes the form of a method of treating an eye condition comprising delivering therapy between a first electrode placed on the eye itself and a second electrode placed behind the ear.

An illustrative, non-limiting example takes the form of a method of treating an eye condition comprising delivering therapy between a first electrode placed on the eye itself and a second electrode placed on the ear.

An illustrative, non-limiting example takes the form of a method of treating an eye condition comprising delivering therapy between a first electrode placed on the eye itself and a second electrode placed on the neck.

An illustrative, non-limiting example takes the form of a method of treating an eye condition comprising delivering therapy between a first electrode placed on the eye itself and a second electrode placed on the back of the head.

An illustrative, non-limiting example takes the form of a method of treating an eye condition comprising delivering therapy between a first electrode placed on the eye itself and a second electrode placed on the chest, shoulder or back.

An illustrative, non-limiting example takes the form of a method of treating an eye condition comprising delivering therapy between a first electrode placed on the eye itself and a second electrode placed on the torso.

An illustrative, non-limiting example takes the form of a method of treating an eye condition comprising delivering therapy between a first electrode placed on the eye itself and a second electrode placed on a limb.

An illustrative, non-limiting example takes the form of a method of treating an eye condition comprising delivering therapy between a first electrode placed on the eye itself and a second electrode placed on an extremity.

An illustrative, non-limiting example takes the form of a method of treating an eye condition comprising delivering therapy between a first electrode placed in the nasal cavity and a second electrode placed behind the ear.

An illustrative, non-limiting example takes the form of a method of treating an eye condition comprising delivering therapy between a first electrode placed in the nasal cavity and a second electrode placed on the ear.

An illustrative, non-limiting example takes the form of a method of treating an eye condition comprising delivering therapy between a first electrode placed in the nasal cavity and a second electrode placed on the neck.

An illustrative, non-limiting example takes the form of a method of treating an eye condition comprising delivering therapy between a first electrode placed in the nasal cavity and a second electrode placed on the back of the head.

An illustrative, non-limiting example takes the form of a method of treating an eye condition comprising delivering therapy between a first electrode placed in the nasal cavity and a second electrode placed on the chest, shoulder or back.

An illustrative, non-limiting example takes the form of a method of treating an eye condition comprising delivering therapy between a first electrode placed in the nasal cavity and a second electrode placed on the torso.

An illustrative, non-limiting example takes the form of a method of treating an eye condition comprising delivering therapy between a first electrode placed in the nasal cavity and a second electrode placed on a limb.

An illustrative, non-limiting example takes the form of a method of treating an eye condition comprising delivering therapy between a first electrode placed in the nasal cavity and a second electrode placed on an extremity.

An illustrative, non-limiting example takes the form of a method of treating an eye condition comprising delivering therapy between a first electrode placed in the nasolacrimal duct and a second electrode placed behind the ear.

An illustrative, non-limiting example takes the form of a method of treating an eye condition comprising delivering therapy between a first electrode placed in the nasolacrimal duct and a second electrode placed on the ear.

An illustrative, non-limiting example takes the form of a method of treating an eye condition comprising delivering therapy between a first electrode placed in the nasolacrimal duct and a second electrode placed on the neck.

An illustrative, non-limiting example takes the form of a method of treating an eye condition comprising delivering therapy between a first electrode placed in the nasolacrimal duct and a second electrode placed on the back of the head.

An illustrative, non-limiting example takes the form of a method of treating an eye condition comprising delivering therapy between a first electrode placed in the nasolacrimal duct and a second electrode placed on the chest, shoulder or back.

An illustrative, non-limiting example takes the form of a method of treating an eye condition comprising delivering therapy between a first electrode placed in the nasolacrimal duct and a second electrode placed on the torso.

An illustrative, non-limiting example takes the form of a method of treating an eye condition comprising delivering therapy between a first electrode placed in the nasolacrimal duct and a second electrode placed on a limb.

An illustrative, non-limiting example takes the form of a method of treating an eye condition comprising delivering therapy between a first electrode placed in the nasolacrimal duct and a second electrode placed on an extremity.

These monopolar examples may, where relevant, comprise crossing from one side of anatomical midline to another, such as by delivering therapy between an electrode on the left superior eyelid and an electrode behind the right ear.

As noted, in general, any combination of pulse generator housing types and electrode types may be used in these bipolar and monopolar examples, to treat any of a range of conditions. Each example is open ended, so the use of third and further electrodes is also an option and may be included in any of these examples. A single facial electrode may be used with two return electrodes (such as by having a combination of an superior eyelid electrode on the left eye sourcing current to or sinking current from electrodes at each of the left and right ears), where variation in current allocation or voltage levels among the three (or more) electrodes can be used to manipulate the spatial characteristics of the therapy.

Another illustrative, non-limiting example takes the form of an apparatus for treating a condition of the eye comprising a pulse generator coupled to a plurality of electrodes, the pulse generator comprising circuitry including a controller configured to perform any of the above illustrative non-limiting example bipolar or monopolar therapy methods. The apparatus may further comprise a headband that holds the pulse generator. Additionally or alternatively, the headband further holds the first and second electrodes in desired positions on the forehead of the patient. Additionally or alternatively, the apparatus may comprise an earpiece adapted to couple onto the ear of the patient, the pulse generator being carried by the earpiece. Additionally or alternatively, the apparatus may comprise an armband adapted to be carried on an arm of the patient, the pulse generator being carried by the armband. Additionally or alternatively, the apparatus may comprise a neckpiece adapted to be worn on the neck of the patient, the pulse generator being carried by the neckpiece. Additionally or alternatively, the apparatus may comprise a frame having an earpiece and a noserest, the pulse generator being carried by the frame. Additionally or alternatively, the apparatus may comprise a harness wearable on the torso of the patient, pulse generator being carried by the harness.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus for treating a condition of the eye comprising a pulse generator coupled to an electrode carrier that carries a plurality of electrodes, the pulse generator comprising circuitry including a controller configured to perform a method of treating an eye condition by delivery of therapy between at least first and second electrodes, wherein the first and second electrodes are carried on the electrode carrier such that when the electrode carrier is worn by a patient, the first electrode is placed above the eye, and the second electrode is placed below the eye, and current passes between the superiorly positioned first electrode and the inferiorly positioned second electrode, wherein the electrode carrier is configured to position the first electrode on the forehead.

2. The apparatus as in claim 1 further comprising an earpiece adapted to couple onto the ear of the patient, the pulse generator being carried by the earpiece.

3. The apparatus as in claim 1 further comprising a frame having an earpiece and a noserest, the pulse generator being carried by the frame.

4. The apparatus as in claim 1 further comprising a third electrode and the pulse generator is configured to use the first, second and third electrodes to issue therapy and/or diagnostic electrical outputs.

5. The apparatus as in claim 4, wherein the third electrode is placed behind the ear.

6. The apparatus as in claim 4, wherein the third electrode is placed on the ear.

7. The apparatus as in claim 4, wherein the third electrode is placed on a housing that holds the pulse generator, the housing being wearable about the neck of a patient to place the third electrode in contact with patient skin.

8. The apparatus as in claim 4, wherein the pulse generator is further configured to deliver therapy in a spatial pattern using the first second and third electrodes to issue therapy with at least first and second steps, wherein utilization of the first, second and third electrodes varies from the first to the second step.

9. The apparatus as in claim 8 wherein the utilization varies as follows:
- in the first stage, first total current is issued by the first and second electrodes to the third electrode, with the first electrode issuing a first percentage of the first total current and the second electrode issuing a second percentage of the first total current;
- in the second stage, second total current is issued by the first and second electrodes to the third electrode, with the first electrode issuing a third percentage of the second total current and the second electrode issuing a fourth percentage of the second total current.

10. The apparatus as in claim 9, wherein the pulse generator is configured such that the first and second total currents are not equal to one another.

11. The apparatus as in claim 1, wherein at least one of the first or second electrodes is an electrode having a gel surface providing conduction through the skin of a user and at least partial adhesion thereto.

12. The apparatus as in claim 1, wherein at least one of the first or second electrodes is a bare metal electrode.

13. The apparatus as in claim 1, wherein at least one of the first or second electrodes is a dry electrode having a plurality of layers including at least metal and flexible polymer layers.

14. A method of treating an eye condition using an apparatus comprising a pulse generator coupled to a plurality of electrodes, the plurality of electrodes comprising at least a first electrode disposed superior to an eye of a patient and a second electrode disposed inferior to the eye of the patient, the method comprising issuing an electrical therapy pulse between the first and second electrodes to generate a current that passes between the superiorly positioned first electrode and the inferiorly positioned second electrode, wherein the electrode carrier is configured to position the first electrode on the forehead and the electrical therapy pulse is issued while the first electrode is on the forehead of the patient.

15. The method of claim 14, wherein the first and second electrodes are disposed on an electrode carrier that holds the first and second electrodes in respective superior and inferior positions.

16. The method of claim 14, wherein the plurality of electrodes further includes a third electrode placed behind the ear of the patient, and pulse generator is configured to use the first, second and third electrodes to issue therapy and/or diagnostic electrical outputs.

17. The method of claim 14, wherein the eye condition is retinitis pigmentosa.

18. The method of claim 14, wherein the step of issuing an electrical therapy pulse includes issuing the electrical therapy pulse with a predetermined amplitude, and the method further comprises determining a phosphene threshold amplitude at which the patient observes phosphenes in response to pulses delivered at the threshold amplitude, and setting the predetermined amplitude relative to the phosphene threshold amplitude.

19. The apparatus as in claim 1, wherein pulse generator is configured to issue therapy pulses between the first and second electrodes at a predetermined amplitude configured to cause the patient to experience phosphenes.

* * * * *